United States Patent
Kashkarov et al.

(10) Patent No.: US 8,734,479 B2
(45) Date of Patent: May 27, 2014

(54) EMBOLUS BLOOD CLOT FILTER DELIVERY SYSTEM

(75) Inventors: Alexander Germanovich Kashkarov, St. Petersburg (RU); Andrzej J. Chanduszko, Chandler, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 1683 days.

(21) Appl. No.: 12/096,783

(22) PCT Filed: Dec. 29, 2006

(86) PCT No.: PCT/US2006/062725
§ 371 (c)(1),
(2), (4) Date: Aug. 20, 2009

(87) PCT Pub. No.: WO2007/079410
PCT Pub. Date: Jul. 12, 2007

(65) Prior Publication Data
US 2009/0318951 A1  Dec. 24, 2009

Related U.S. Application Data

(60) Provisional application No. 60/754,636, filed on Dec. 30, 2005.

(51) Int. Cl.
*A61M 29/00* (2006.01)

(52) U.S. Cl.
USPC ....................................................... 606/200

(58) Field of Classification Search
USPC ........ 606/1, 191–200; 128/898–899; 600/200
See application file for complete search history.

(56) References Cited

U.S. PATENT DOCUMENTS

| | | | |
|---|---|---|---|
| 4,425,908 A | | 1/1984 | Simon |
| 4,494,531 A | | 1/1985 | Gianturco |
| 4,688,553 A | * | 8/1987 | Metals .......................... 128/899 |
| 5,108,418 A | | 4/1992 | Lefebvre |
| 5,669,933 A | * | 9/1997 | Simon et al. .................. 600/200 |
| 5,709,704 A | | 1/1998 | Nott et al. |
| 5,776,162 A | | 7/1998 | Kleshinski |

(Continued)

FOREIGN PATENT DOCUMENTS

| | | |
|---|---|---|
| EP | 188927 B1 | 7/1989 |
| WO | WO 2006/124405 A2 | 11/2006 |
| WO | WO 2007/021340 A1 | 2/2007 |

OTHER PUBLICATIONS

International Search Report, PCT/US2006/062725.

(Continued)

*Primary Examiner* — Katherine Dowe
*Assistant Examiner* — Sidharth Kapoor
(74) *Attorney, Agent, or Firm* — Garvey, Smith, Nehrbass & North, L.L.C.; Seth M. Nehrbass; Charles C. Garvey, Jr.

(57) ABSTRACT

A blood filter delivery system for delivering a blood filter into a vein includes a push rod for pushing the blood filter through and out of a catheter, the push rod having a filter positioning assembly on one end. The filter positioning assembly includes positioner members, which retain anchor members of the filter. The filter positioning assembly can position the end of the delivery catheter near the blood vessel centerline before releasing the filter's anchor members, thereby helping to align the blood filter along the centerline of the blood vessel.

29 Claims, 25 Drawing Sheets

(56) References Cited

U.S. PATENT DOCUMENTS

| | | | |
|---|---|---|---|
| 5,800,457 A | 9/1998 | Gelbfish | |
| 5,836,968 A | 11/1998 | Simon et al. | |
| 6,007,558 A | 12/1999 | Ravenscroft et al. | |
| 6,080,178 A | 6/2000 | Meglin | |
| 6,156,055 A * | 12/2000 | Ravenscroft | 606/206 |
| 6,176,871 B1 | 1/2001 | Pathak et al. | |
| 6,193,739 B1 * | 2/2001 | Chevillon et al. | 606/200 |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,331,183 B1 | 12/2001 | Suon | |
| 6,436,120 B1 | 8/2002 | Meglin | |
| 6,443,972 B1 | 9/2002 | Bosma et al. | |
| 6,468,290 B1 | 10/2002 | Weldon et al. | |
| 6,540,767 B1 | 4/2003 | Walak et al. | |
| 6,589,266 B2 | 7/2003 | Whitcher et al. | |
| 6,623,506 B2 | 9/2003 | McGuckin, Jr. et al. | |
| 6,872,217 B2 | 3/2005 | Walak et al. | |
| 7,056,286 B2 | 6/2006 | Ravenscroft et al. | |
| 2001/0003796 A1 | 6/2001 | Yang et al. | |
| 2001/0039432 A1 | 11/2001 | Whitcher et al. | |
| 2003/0071285 A1 | 4/2003 | Tsukernik | |
| 2003/0074019 A1 | 4/2003 | Gray et al. | |
| 2003/0187495 A1 | 10/2003 | Cully et al. | |
| 2004/0073252 A1 | 4/2004 | Goldberg et al. | |
| 2004/0186512 A1 | 9/2004 | Bruckheimer et al. | |
| 2004/0193209 A1 | 9/2004 | Pavcnik et al. | |
| 2005/0055045 A1 | 3/2005 | DeVries et al. | |
| 2005/0085847 A1 | 4/2005 | Galdonik et al. | |
| 2005/0159771 A1 | 7/2005 | Petersen | |
| 2005/0159773 A1 | 7/2005 | Broome et al. | |
| 2005/0163821 A1 | 7/2005 | Sung et al. | |
| 2005/0177224 A1 | 8/2005 | Fogarty et al. | |
| 2005/0222604 A1 * | 10/2005 | Schaeffer | 606/200 |
| 2005/0234503 A1 | 10/2005 | Ravenscroft et al. | |
| 2005/0277977 A1 | 12/2005 | Thornton | |
| 2006/0036279 A1 | 2/2006 | Eidenschink et al. | |
| 2006/0095068 A1 | 5/2006 | WasDyke et al. | |
| 2006/0106417 A1 * | 5/2006 | Tessmer et al. | 606/200 |

OTHER PUBLICATIONS

International Preliminary Report on Patentability and Written Opinion of the International Searching Authority in PCT/US06/62725.

* cited by examiner

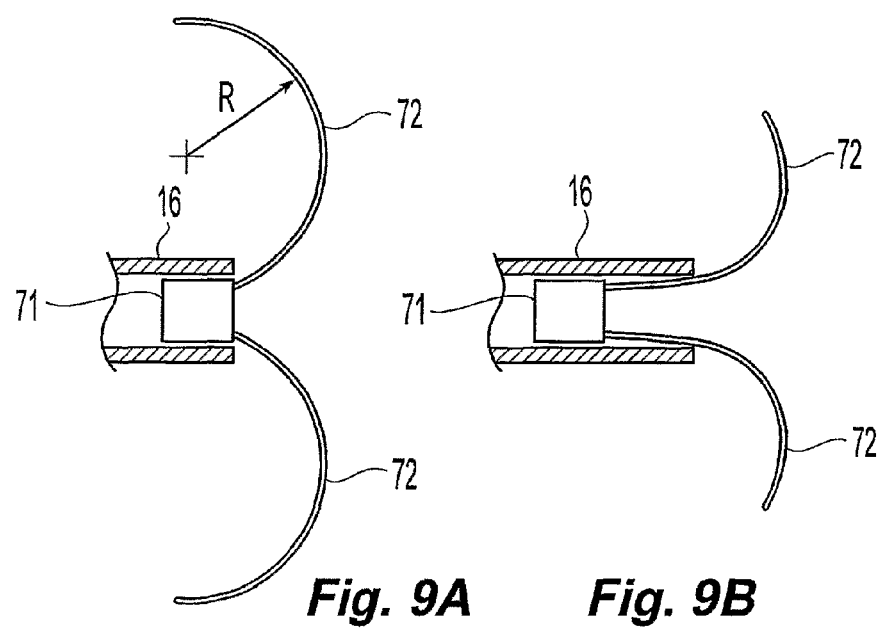
*Fig. 9A*  *Fig. 9B*
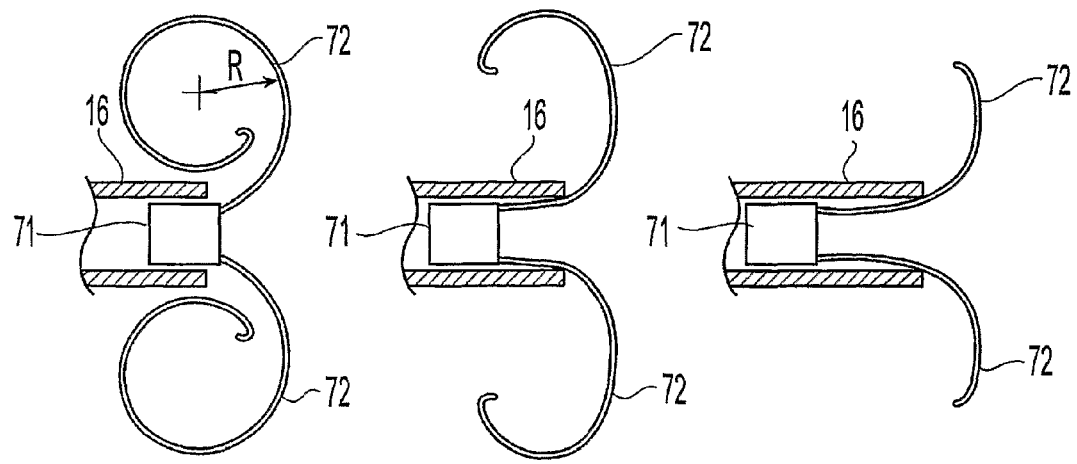
*Fig. 9C*  *Fig. 9D*  *Fig. 9E*

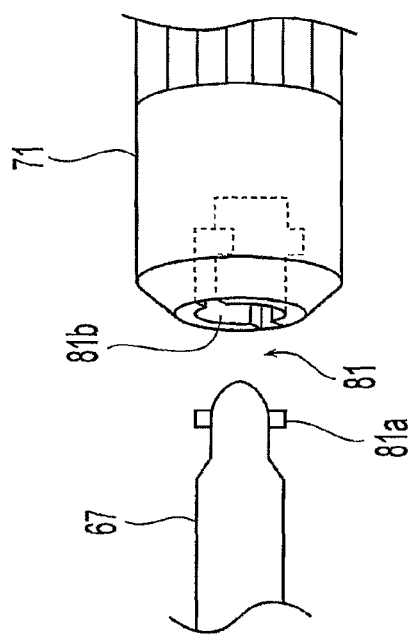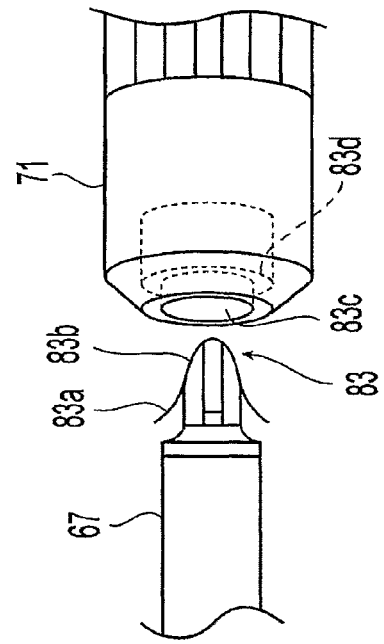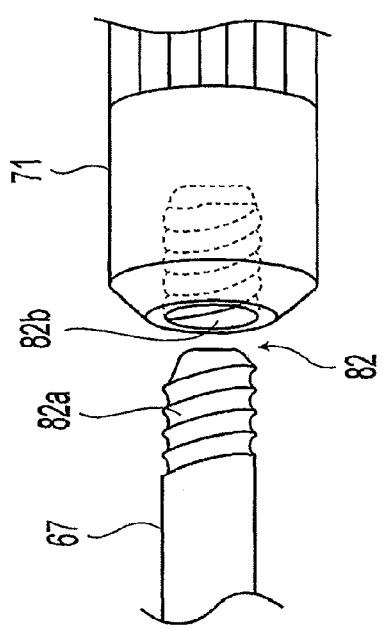

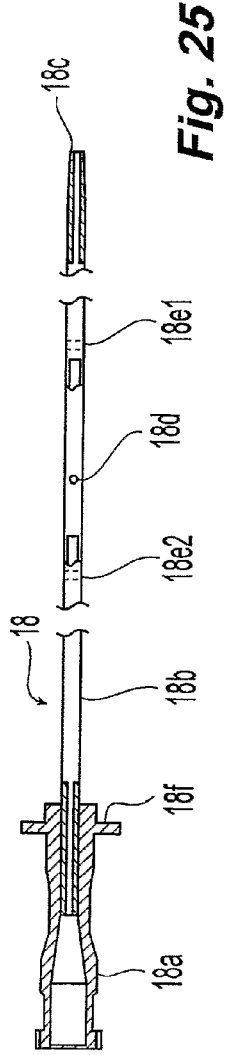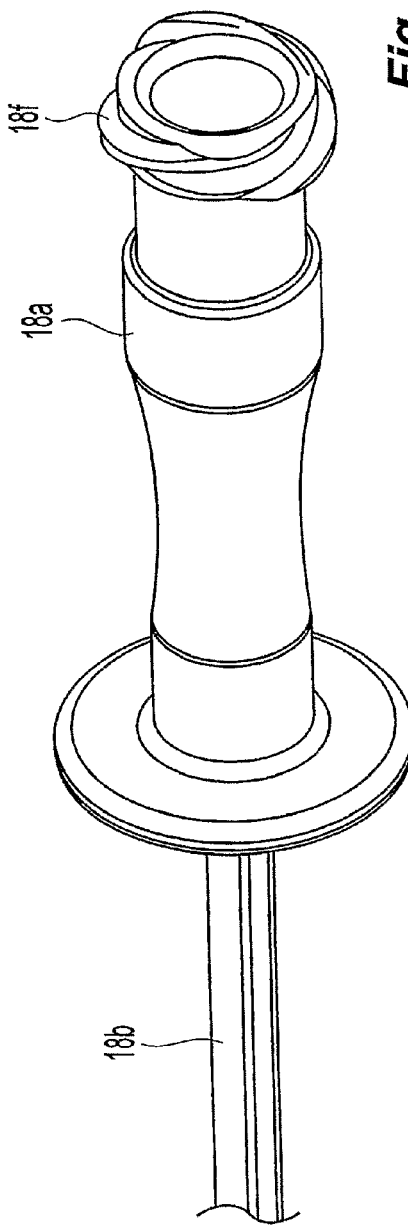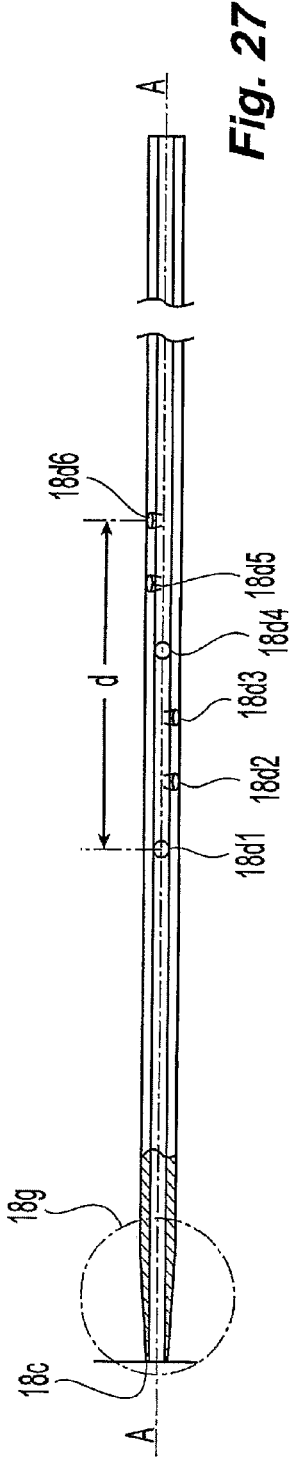

EMBOLUS BLOOD CLOT FILTER DELIVERY SYSTEM

PRIORITY DATA AND INCORPORATION BY REFERENCE

This is a National Stage application under 35 U.S.C. 371 of International Application No. PCT/US2006/062725, filed Dec. 29, 2006, which claims the benefit of priority to U.S. Provisional Patent Application No. 60/754,636, filed Dec. 30, 2005 each of which is incorporated by reference in its entirety. This invention is related to the subject matter shown and described in the following: (i) PCT International Application No. PCT/US06/62722, filed Dec. 29, 2006, entitled "Removable Blood Clot Filter with Edge For Cutting Through the Endothelium" and claiming the benefit of priority to U.S. Provisional Patent Application No. 60/754,600, filed Dec. 30, 2005; (ii) PCT International Application No. PCT/US06/62719, filed Dec. 29, 2006, entitled "Embolus Blood Clot Filter with Post Delivery Actuation," and claiming the benefit of priority to U.S. Provisional Patent Application No. 60/754,633, filed Dec. 30, 2005; (iii) PCT International Application No. PCT/US06/62733, filed Dec. 29, 2006, entitled "Embolus Blood Clot Filter Removal System and Method," and claiming the benefit of priority to U.S. Provisional Patent Application No. 60/754,598, filed Dec. 30, 2005; (iv) PCT International Application No. PCT/US06/62720, filed Dec. 29, 2006, entitled "Embolus Blood Clot Filter with Floating Filter Basket," and claiming the benefit of priority to U.S. Provisional Patent Application No. 60/754,599, filed Dec. 30, 2005; and (v) PCT International Application No. PCT/US06/62730, filed Dec. 29, 2006, entitled "Embolus Blood Clot Filter with Bio-Resorbable Coated Filter Members," and claiming the benefit of priority to U.S. Provisional Patent Application No. 60/754,597, entitled "Embolus Blood Clot Filter with Retainers on Locator Filter Members," filed Dec. 30, 2005, each of which is hereby incorporated by reference in its entirety.

TECHNICAL FIELD

This invention relates to a device for delivering a blood filter into a vessel of a patient's body to reduce the risk of embolisms.

BACKGROUND ART

In recent years, a number of medical devices have been designed which are adapted for compression into a small size to facilitate introduction into a vascular passageway and which are subsequently expandable into contact with the walls of the passageway. These devices include, among others, blood clot filters, which expand and are held in position by engagement with the inner wall of a vein, such as the vena cava. These vena cava filters are generally designed to remain in place permanently. Typically, blood filters are made of metal wire in a configuration designed to fill the cross section of the blood vessel with filter members. Such filters must be radially compressed to fit within a delivery catheter, and these filters include structure to anchor the filter in place within the vena cava, such as elongate diverging anchor members with hooked ends that penetrate the vessel wall and positively prevent longitudinal migration of the filter in either direction within the vessel.

Known systems and methods for delivering a blood filter to a location in a patient's blood vessel are disclosed, such as in U.S. Pat. No. 6,258,026, which is hereby incorporated by reference in its entirety. Typically, a filter delivery catheter is positioned within a patient's blood vessel by threading it through a major vein or artery from a point of access, such as the jugular or femoral veins. Once the distal end of the catheter is in position where the filter is to be delivered, the blood filter is placed in the proximal end of the catheter and pushed through to the distal end by a pusher member, such as a stiff wire. When the filter is pushed out of the distal end of the catheter, the filter members spring radially outward to contact the blood vessel's wall. The hooked ends of the anchor members engage the vessel wall and hold the filter in place.

Known systems and methods for installing blood filters have deficiencies and drawbacks. One such deficiency with known delivery devices makes it difficult to align the filter for implantation because there is no self acting mechanism for centering the delivery catheter.

DISCLOSURE OF INVENTION

The various embodiments provide for blood filter delivery systems that alleviate the deficiencies of known delivery systems and filters. In an embodiment, an apparatus for pushing a blood filter from a delivery catheter includes a plurality of positioner or positioning members coupled to the distal end of a push rod assembly. The positioner members are configured so that they will fit over the hooked ends of the filter anchor members, gripping the anchor members when the filter and positioner members are situated in a catheter or storage tube. The positioner members are shaped and coupled to a hub on the push rod assembly so that when they extend beyond the end of the catheter, the positioner members bend away from the centerline of the catheter and push rod assembly. The positioner members are sized and shaped so that their distal ends will contact and push against the blood vessel wall before the filter or the entire positioner member is beyond the end of the catheter. By pressing on the blood vessel wall, the positioner members bring the end of the catheter into near alignment with the centerline of the blood vessel. The positioning action happens before the filter's anchor members are released by the positioner members.

In an embodiment, a filter deliver system includes a catheter and a filter positioning assembly situated within the catheter. The filter positioning assembly includes a hub and a plurality of positioner members coupled to the hub. Each of the plurality of positioner members includes an end that cooperates with and retains the plurality of anchor members within the catheter when the ends of the positioner members are disposed within the catheter.

In another embodiment, a filter delivery assembly for delivering a blood filter having a plurality of anchor members into a blood vessel includes a storage tube within which are positioned a blood filter and a filter positioning assembly. The filter positioning assembly includes a plurality of positioner members forming a retaining boundary that contains the plurality of filter anchor members. An elongated push rod may be coupled to the filter positioning assembly.

Another embodiment is a push rod assembly for use in delivering into a blood vessel via a catheter a blood filter having a plurality of anchor members. The push rod assembly includes a push rod extending along a longitudinal axis from a first end to a second end, a handle disposed proximate the first end, and a filter positioning assembly disposed proximate the second end. The filter positioning assembly has a longitudinal axis and includes a hub and a plurality of positioner members coupled to the hub. Each of the plurality of positioner members is curved and oriented so that the positioner members extend away from the longitudinal axis when unconstrained, and are configured to collapse toward the longitudinal axis so as to retain the plurality of anchor members when the positioner members and blood filter are situated within the catheter.

In another embodiment, a filter delivery system includes at least a catheter introducer, a filter storage tube, a push rod assembly having a filter positioning assembly on its distal end, with the filter positioning assembly including a plurality of anchor retention members. The catheter introducer has a coupling port connected to an elongated generally tubular member. The storage tube is configured to be coupled to the coupling port of the introducer and an adaptor, such as a Touhy-Borst Adapter. The push rod assembly has a first end that may be disposed in the storage tube and a second end extending out of the Touhy-Borst Adapter. The push rod assembly may include a handle, a push wire, and a filter positioning assembly engaged to a blood filter. The handle may be disposed along a longitudinal axis of the push rod assembly proximate the second end. The push rod is disposed along the longitudinal axis proximate the first end of the push rod assembly. The filter positioning assembly is disposed on the distal end of the push rod assembly along the longitudinal axis. In an assembled, pre-delivery configuration, a blood filter, which has a plurality of anchor members disposed about the longitudinal axis each having a hook on the end, is folded into a narrow profile and captured by the filter positioning assembly by folding the positioner members over the anchor members of the filter. The assembled filter and filter positioning assembly are situated within the filter storage tube.

In another embodiment, a method of packaging a blood filter having a plurality of anchor members coupled to a hub and disposed about a longitudinal axis is disclosed. The method includes folding the plurality of anchors generally parallel to the longitudinal axis, enclosing the plurality of anchors within a plurality of positioner members coupled to a push rod assembly, and enclosing the filter and the positioner members in a generally tubular member.

In another embodiment, a method of delivering a blood filter into a blood vessel via a catheter (an end of which is situated within a blood vessel) is disclosed. The method preferably includes pressing against a wall of the blood vessel with a plurality of positioner members, retaining anchor members of the blood filter until the plurality of positioner members exit the catheter, and preventing the anchor members of blood filter from engaging the blood vessel wall until the catheter is positioned in near alignment with the centerline of the blood vessel.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, explain features of the invention.

FIGS. 8A-8C and 9A-9E illustrate various embodiments of the filter positioning assembly of the push rod assembly illustrated in FIG. 6.

FIGS. 14A-14C are detail views of alternative embodiments of the filter positioning assembly and a portion of the push rod assembly of FIG. 6.

FIG. 25 is a side sectional view of a catheter expander suitable for use with various embodiments of the present invention.

FIGS. 26-28 are detail views of portions of the catheter expander of FIG. 25.

MODE(S) FOR CARRYING OUT THE INVENTION

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

The blood filter delivery apparatus and system in the various embodiments mechanically integrate components to safely and reliably deliver and emplace a blood filter within a patient's blood vessel, such as the vena cava. The apparatus and system preferably connects or is prepackaged with a filter in a filter storage tube and assists in properly positioning the filter in the vein in a reliable fashion.

Figure 1:
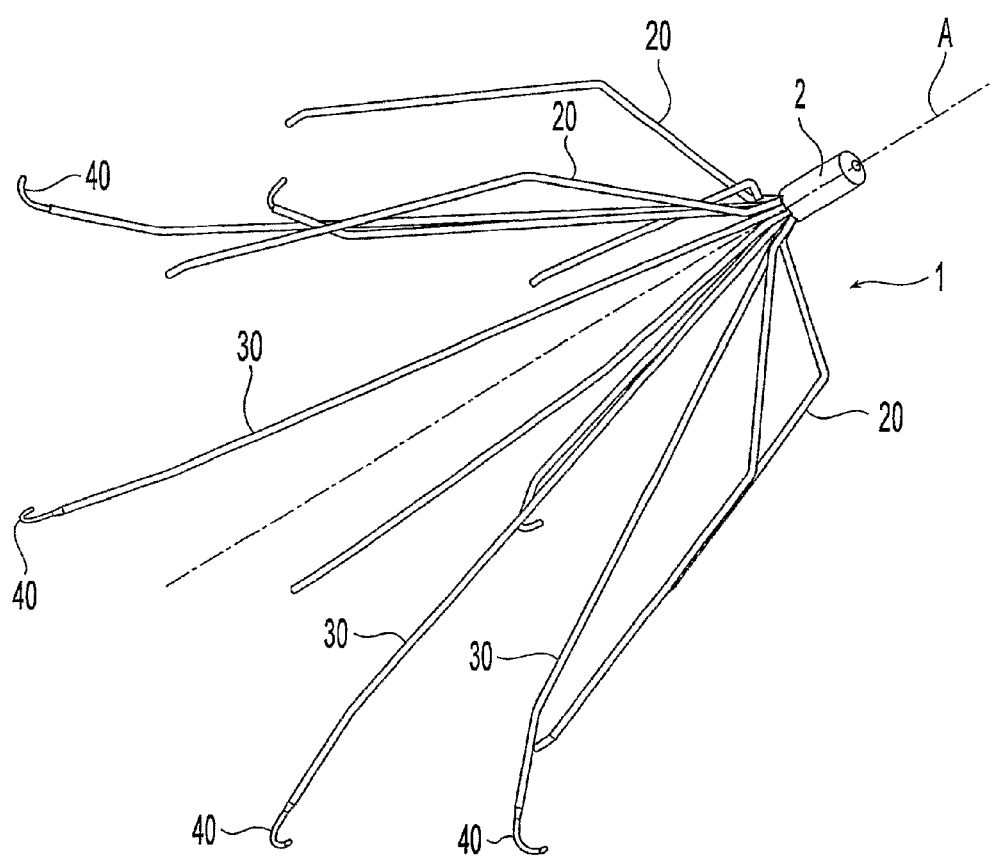
FIG. 1 is a perspective view of an embodiment of a blood filter.

The various embodiments are intended to be used with a variety of blood filters, examples of which are described here to inform the discussion of the embodiments of the present invention. Referring to FIG. 1, a blood filter typically will include a hub 2 to which are coupled a plurality of filter members 20, 30. The filter members 20, 30 both position and anchor the filter 1 in the blood vessel and serve as the filter mesh elements which screen emboli from blood that passes through the filter. Common blood filters include anchor members 30 and locator members 20.

Anchor members 30 can include a hook 40 or hooks near their distal ends (i.e., the ends opposite from the proximal ends, which are coupled to the hub 2). The hooks 40 are designed to penetrate and hook into the endothelial layer of the blood vessel to prevent longitudinal migration of the filter 1 within the vessel. Hooks 40 may have a smaller cross sectional area than the cross sectional area of the anchor members. Anchor members 30 are formed so they flex radially outward, as illustrated in FIG. 1, so their distal ends apply sufficient pressure against the blood vessel wall to drive the hooks 40 into the endothelial tissue. In an example filter, the anchor members have a spread of approximately 1.6 inches (about 40 millimeters) in an unconstrained configuration (i.e., not installed in the blood vessel).

Locator members 20 also are formed so that when they are released from the delivery catheter they flex radially outward so their distal ends press against the blood vessel walls. Without hooks, the locator members' 20 distal ends apply generally equal spring force about the circumference of the vessel wall which, if all locators act together, moves the filter hub 2 toward the vessel's centerline. This centering movement positions the filter for proper expansion of the filter members 20, 30 and helps ensure forces are applied equally to the vessel walls.

Figure 3:
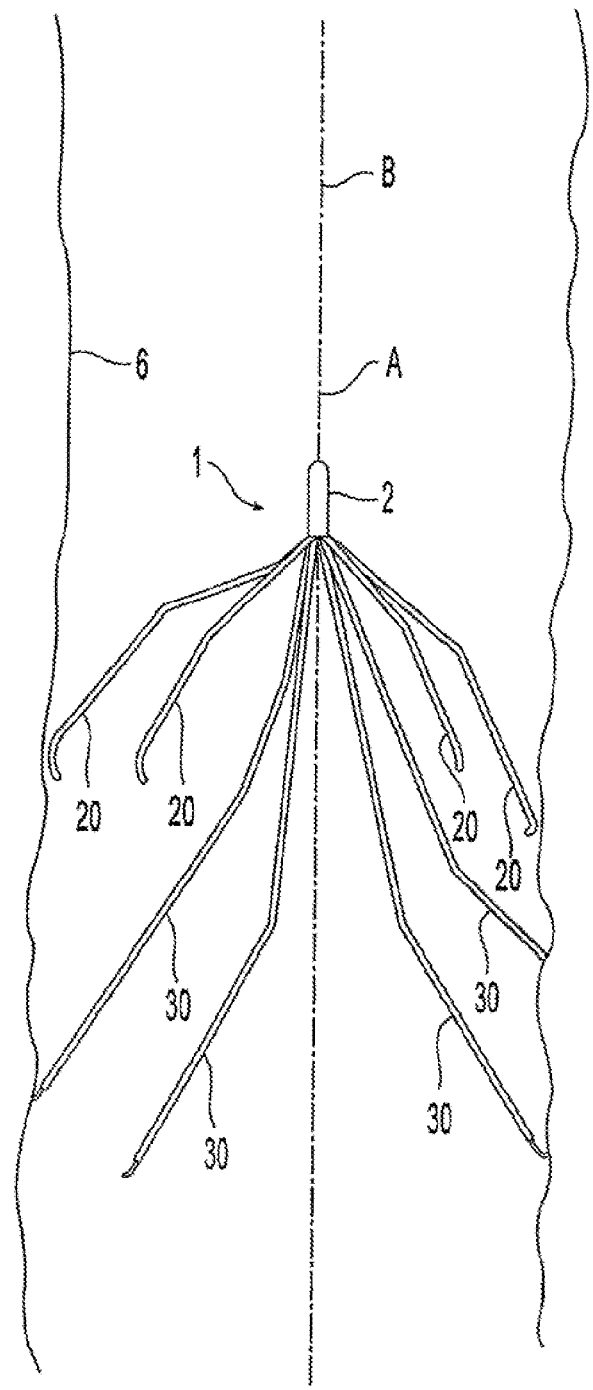
FIG. 3 is a perspective view of the blood filter of FIG. 1 positioned within a blood vessel.

FIG. 3 illustrates a filter installed so its longitudinal axis A is approximately aligned with the centerline B of a blood vessel 6. Positioning the filter 1 so it is aligned with the vessel's centerline B helps to provide proper filter functioning and reduce the potential for injury to the blood vessel's wall due to application of excessive force by any one or a few filter members 20, 30.

Typically, filter locator members 20 are spaced equiangularly about the filter hub 2 so that even spacing exists between the locators 20 to provide an effective filter basket. For the same reason, anchor members 30 are typically positioned equiangularly about the hub 2. To facilitate folding the filter into its narrowest possible profile (illustrated in FIG. 2) for insertion in a delivery catheter, locator members 20 may be angularly offset from the anchor members 30 about the filter hub 2. In this manner, locator members 20 can fit between anchor members 30 in the folded, pre-delivery configuration.

To facilitate filter centering, common blood filters feature locator members 20 that are shorter than the anchor members 30, so that when the filter is ejected from the delivery catheter hub-end first, the locator members 20 deploy before the anchors, thereby centering the filter 1 at a point of equal force on the locator members 20 (i.e., equidistant from the locator member 20 ends) before the anchor members 30 deploy. If the filter 1 is aligned with the vessel centerline B, the filter hub 2 will be positioned at or near the centerline, as illustrated in FIG. 3. This centering-before-anchoring capability is important because the hooks 40 will tend to lock the filter in place once they penetrate the endothelial layer.

Figure 4:
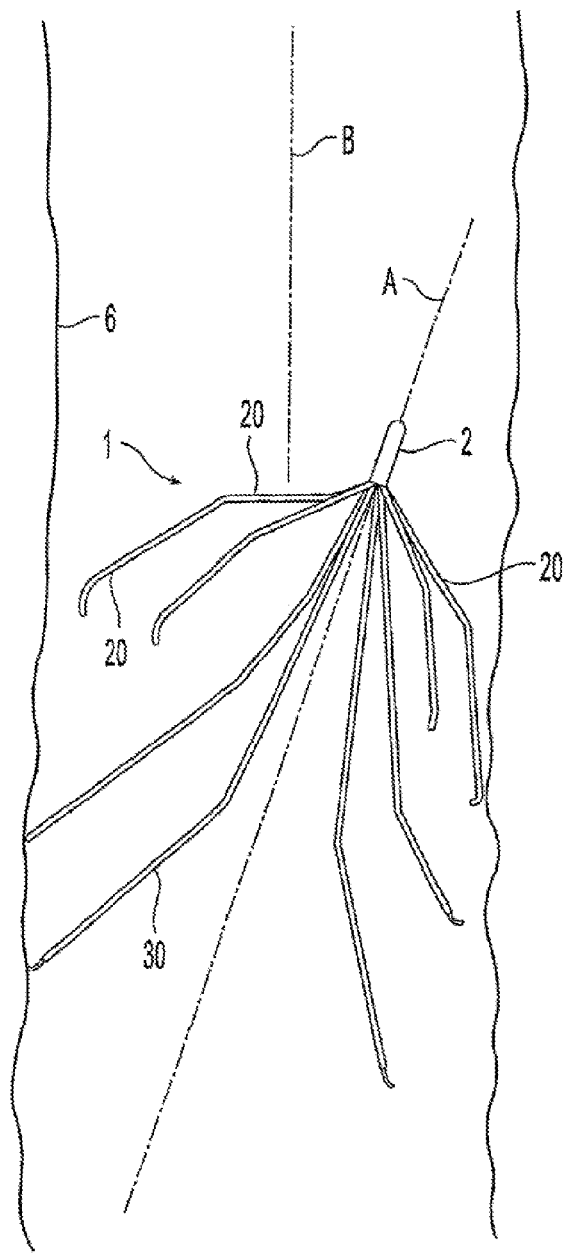
FIG. 4 is a perspective view of the blood filter of FIG. 1 positioned at an angle within a blood vessel.

While deploying the locator members 20 before the anchor members 30 tends to center the filter hub 2 within the blood vessel at a point of equal force on all locator members, this action may not always align the filter with the vessel's centerline. In some circumstances, the filter 1 may be misaligned within the blood vessel 6 so that the filter's longitudinal axis A is at an angle to the vessel's centerline B. If the misalignment is significant enough, such as is illustrated in FIG. 4, the filter 1 may have less filtering volume than a properly aligned filter.

Figure 5:
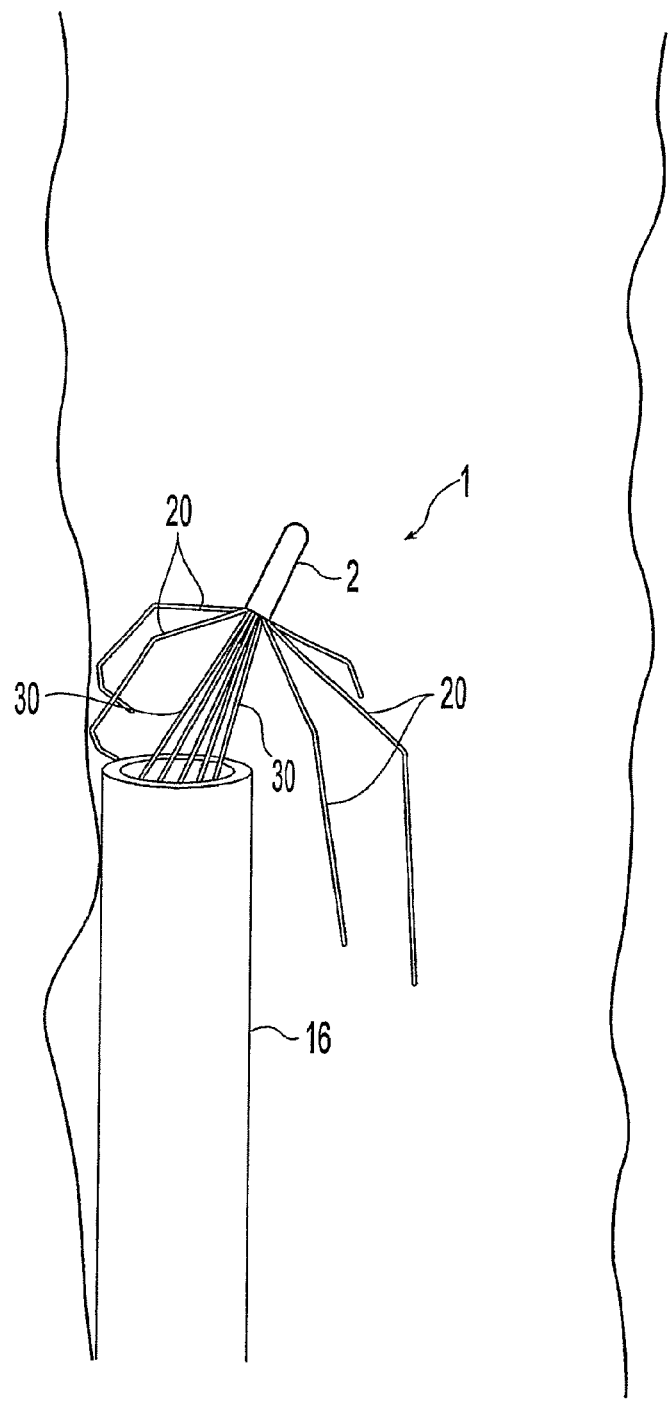
FIG. 5 is a perspective view of the blood filter of FIG. 1 at a stage of delivery to the blood vessel.

Filter misalignment may occur when a filter 1 is delivered into a blood vessel 6 with the catheter 16 positioned against the vessel wall, as illustrated in FIG. 5. Due to a host's vessel anatomy, the end of the catheter 16 may be off center or even resting on a side of the blood vessel when the filter 1 is ejected. As shown in FIG. 5, with the catheter 16 misaligned within the blood vessel 6, the centering force provided by the locator members 20 may contribute to misaligning the filter within the blood vessel. To avoid this condition, a clinician may use fluoroscopy to view the relative position of the catheter 16 in the blood vessel 6. But this step involves additional procedure time and radiation exposure to the patient.

When the end of the catheter 16 is aligned with the vessel's centerline B, the anchor members 30 will tend to spring outward and engage the vessel wall 6 so the entire filter 1 is fixed in an aligned orientation with respect to the vessel's centerline B. The various embodiments provide a capability for centering the catheter's end, without additional clinician efforts, using structure which mechanically centers the catheter within the vessel prior to releasing the anchor members 30.

Figure 6:
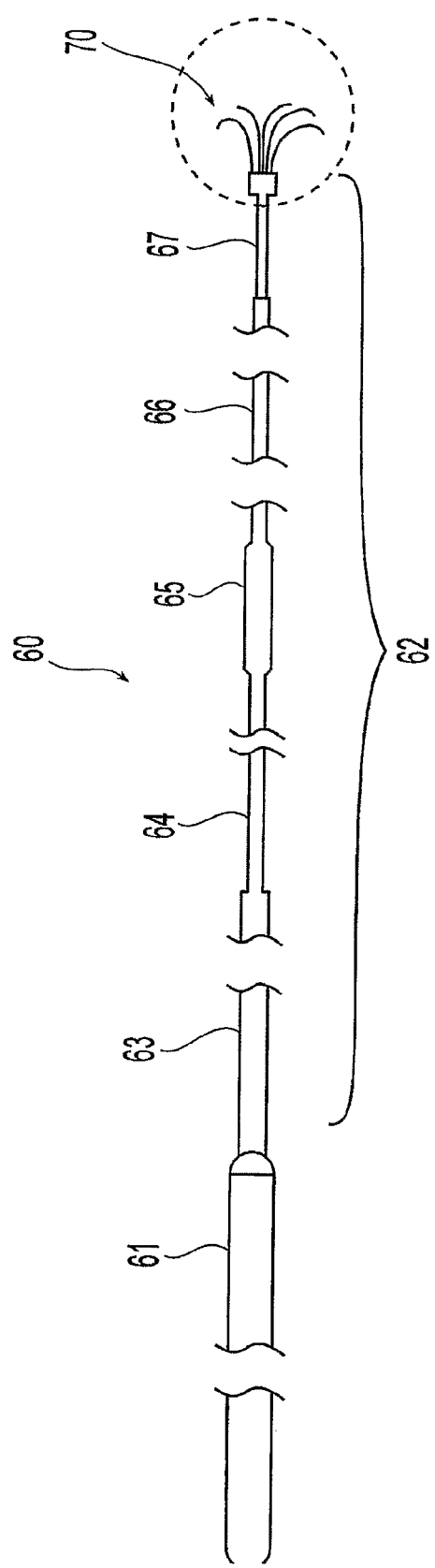
FIG. 6 is a side view of a push rod assembly for delivering a filter of the type illustrated in FIG. 1 into a blood vessel.

Referring to FIG. 6, shown is a preferred elongated push rod assembly 60 for advancing a filter 1 through a delivery catheter 16. The push rod assembly 60 may include a handle 61 coupled to the proximal end, an extended portion 62 which may feature a number of elements of different lengths and cross sections 63-67, and a filter positioning assembly 70 coupled to the distal end of the push rod 60. The push rod assembly 60 has a longitudinal length preferably in the range from about 12 inches (about 300 mm) to about 40 inches (about 1020 mm), and is preferably about 36 inches (about 910 mm).

The various elements of the push rod assembly 60 may be made from different materials. For example, the handle 61 may be formed of a number of metallic, polymer or plastic materials, and is preferably formed from PEBA, which is coupled to a stainless steel hollow section 63 having a diameter of about 0.041 inches. The hollow stainless steel tube 63 may be connected to a suitable alloy material wire 64, including, for example, a super-elastic shape memory alloy (e.g., Nitinol), on which various elements can be disposed, such as a stop or boss portion 65. The shape memory alloy can further be defined as preferably having an austenite finish ($A_f$) temperature below body temperature. The stainless steel hollow section 63 may be coupled to an extended wire 64, which may be made from stainless steel, the Cobalt-Chromium-Nickel alloy known as Elgiloy®, or a super-elastic shape memory alloy, such as Nitinol. A terminal portion 67, positioned at the distal end of the extended portion 62, may have a smaller diameter than the wire 64, 66 and can be made from stainless steel or Elgiloy®, and more preferably is made of Nitinol. In a preferred embodiment, the terminal portion 67 has a diameter of about 0.020 inches.

Figure 7A:
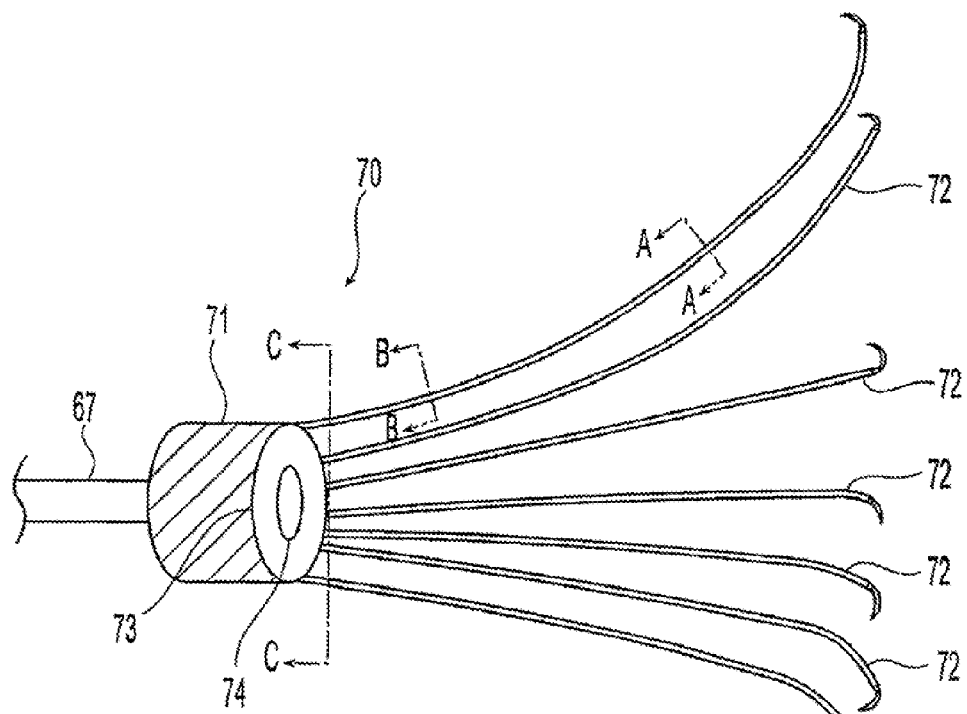
FIG. 7A is a detail view of the filter positioning assembly of the push rod assembly of FIG. 6.

Coupled to the terminal portion 67 is a filter positioning assembly 70 which is configured to push the filter 1 through a delivery catheter 16, position the end of the catheter near the center of the blood vessel after the filter's locator members 20 deploy and delay release of the anchor members 30 until after the catheter end is centered. Referring to FIG. 7A, the filter positioning assembly 70 includes a hub 71 coupled on one end to the terminal portion 67 of the push rod 60. On the other end, the hub 71 is coupled to a number of positioner members 72 which function to: (1) position the end of the catheter at or near the centerline of the blood vessel; and/or (2) retain filter anchor members in a collapsed configuration until the catheter end has been centered.

Figure 2:
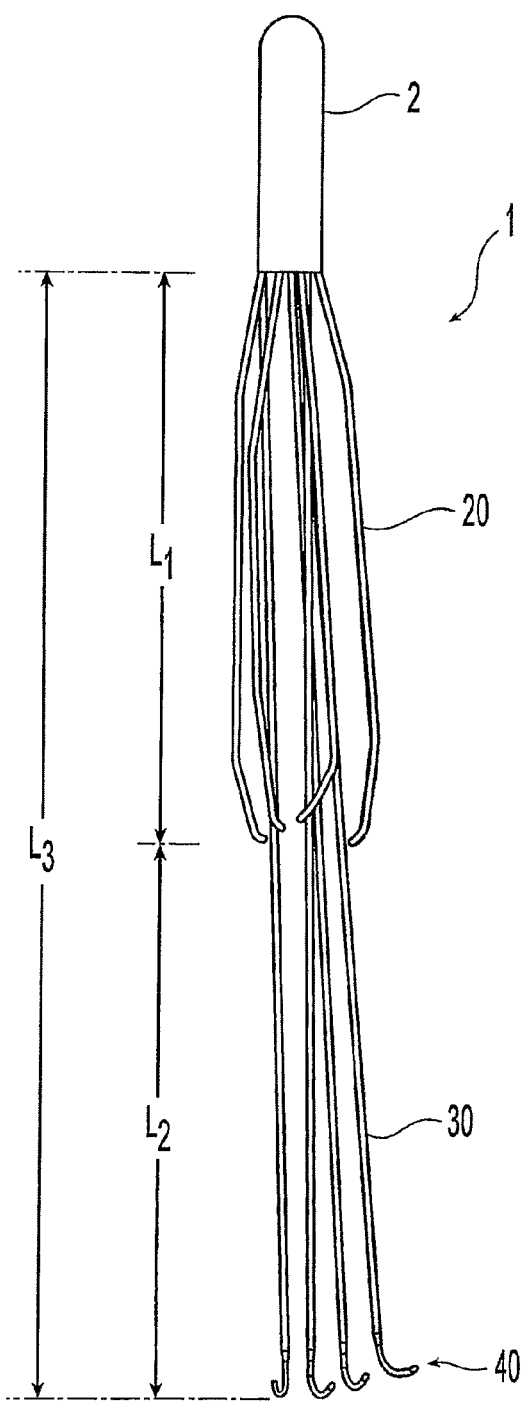
FIG. 2 is a side perspective view of the filter of FIG. 1 in a folded configuration.
Figure 11:
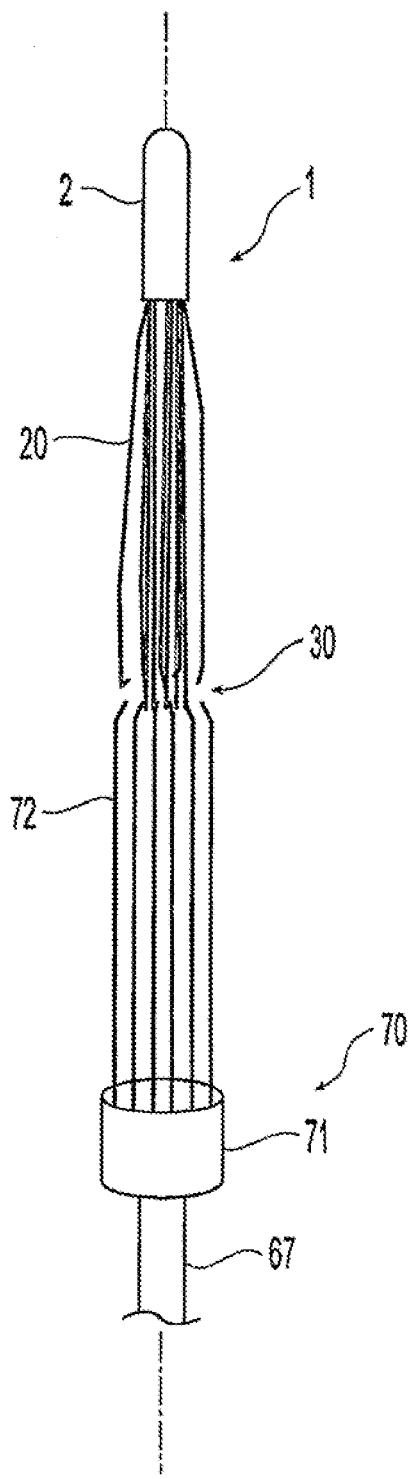
FIG. 11 is a side view of a filter and the filter positioning assembly of the push rod assembly of FIG. 6.
Figure 12:
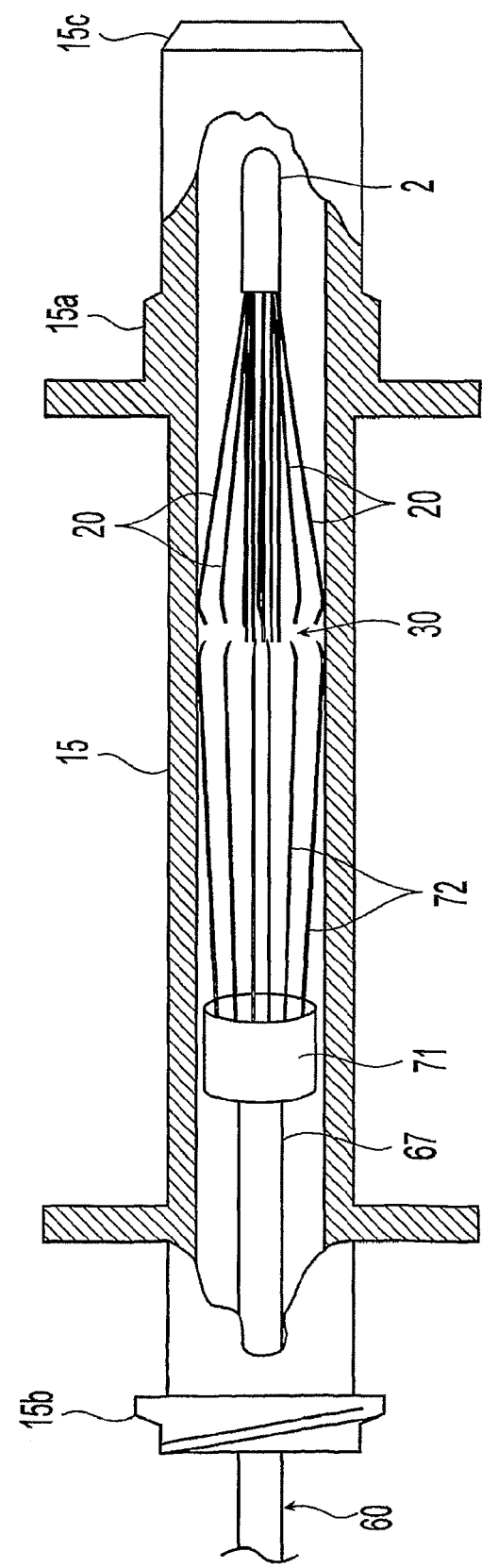
FIG. 12 is a sectional view of a filter storage tube including a filter and filter positioning assembly.

Within the storage tube 15 and delivery catheter 16, the positioner members 72 fold down over the filter anchor members 30 when the filter is in the folded configuration illustrated in FIG. 2 to present a narrow profile assembly as illustrated in FIG. 11. For some embodiments, though not all, there is one positioner member 72 for each anchor member 30 in the filter 1, and the filter 1 and the positioner members 72 are aligned so each positioner lies on top of one anchor member 30. When folded over the filter so the positioner members 72 will fit within the storage tube 15 or a delivery catheter 16, as illustrated in FIGS. 11 and 12, the positioner members 72 can provide means to encircle the anchor members 30 thereby retaining the anchor members. In the folded configuration within the storage tube 15 or delivery catheter 16, the positioner members 72 lie approximately parallel to the longitudinal axis of the filter 1 and filter positioning assembly 70.

In an embodiment, positioner members 72 in the folded configuration grip the anchor members 30 sufficiently so that the pushing force required to push the filter 1 through the delivery catheter 16 by the push rod 60 is transferred from the positioner members 72 to the anchor members 30 and then to the filter hub 2. As illustrated in FIG. 11, the positioner members 72 may be sized to cover the anchor members 30 up to the point where the locator members 20 overlap the anchor members 30 in the folded configuration. Thus, for example, referring to filter 1 of FIG. 2, the positioner members 72 of the assembly 70 are preferably defined by a length equal to $L_2$, which is the difference between the locator member length $L_1$ and the anchor member length $L_3$ in the folded configuration of the filter 1. The locator member length $L_1$ and anchor member length $L_3$ can be any length suitable for use as an implantable device. Preferably, length $L_1$ can be from about 24 millimeters (about 0.95 inches) to about 37 millimeters (about 1.5 inches) and length $L_3$ can be from about 36 millimeters (about 1.4 inches) to about 52 millimeters (about 2 inches).

In an embodiment, the plurality of positioner members 72 are joined at their proximal ends to the hub's periphery so that a pushing surface 73 is formed on the hub 71, as shown in FIG. 7A. A central lumen 74 is provided through the hub 71 and terminal portiob 67 so that other implements (e.g., guidewire, borescope, saline, contrast agents and so on) can be transported from the proximal end of the catheter to the distal end of the catheter.

In an embodiment, the hub 71 includes or is made of a radio-opaque material, which facilitates determining the location of the filter using fluoroscopy. As used herein, a radio-opaque marker is any material that is identifiable to machine or human readable radiographic equipment while the material is inside a patient's body, such as, by way of example, but not by way of limitation, gold, platinum, barium sulfate, or tantalum.

Figure 18:
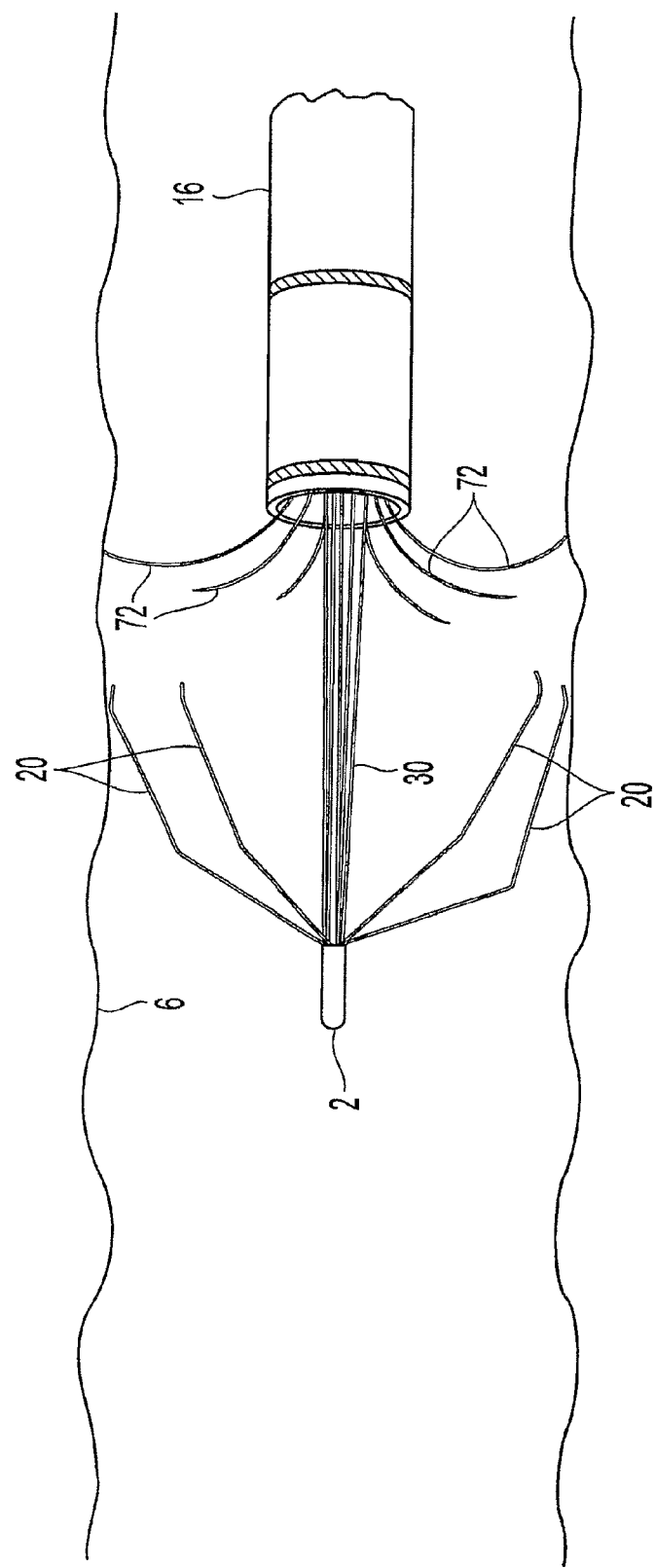

The positioner members 72 preferably have a curved shape when unconstrained, as illustrated in FIG. 7A, with a length and curvature configured so that when the positioner members 72 are partially beyond the end of the delivery catheter 16 their distal ends are in contact with the walls of the blood vessel, as illustrated in FIG. 18. Accordingly, as the positioning assembly 70 exits the end of the delivery catheter 16, the tips of the positioner members 72 bend radially outward and preferably away from the central lumen 74. The positioner members 72 are further configured so that they apply a spring force against the vessels walls when they contact the walls to position the end of the catheter near the blood vessel's centerline. The positioner members 72 are further configured so that when they are fully beyond the end of the catheter, the members bend away from the longitudinal axis (i.e., open) enough to release the plurality of anchor members 30 of the filter 1. Thus, the size and shape of the positioner members 72 will vary depending upon the internal diameter of the blood vessel into which a filter is to be delivered, just as the sizes and orientations of filter locator and anchor members 20, 30 depend upon the size of the intended blood vessel. Descriptions of various alternative positioner member 72 shape and configuration embodiments are provided below with reference to FIGS. 8A-C and 9A-E.

When the ends of the positioner members 72 press against the vessel wall, the resulting spring force is transferred to the hub 71, and thereby provide a means to pus the hub 71—and with it the end of the catheter 16—toward the point of equal force among the various positioner members 72, which will normally be at or near the centerline of the blood vessel. In order to hold the positioner members 72 in their flexed configuration and receive the applied force, the positioner members 72 must be securely coupled to the hub 71. The positioner members 72 may be so coupled to the hub 71 by welding or brazing, or the hub 71 and positioner members 72 may be machined from a single piece, such as, for example, by removing the center portion down to the surface 73 followed by cutting out thin strips of metal (e.g., Nitinol or Elgiloy®) to form the positioner members 72. As shown in FIGS. 7C and 7D, a unitary positioner assembly 70B can be provided by cutting a generally tubular stock 70A to provide for the positioner members 72 and a central lumen.

Figure 7B:
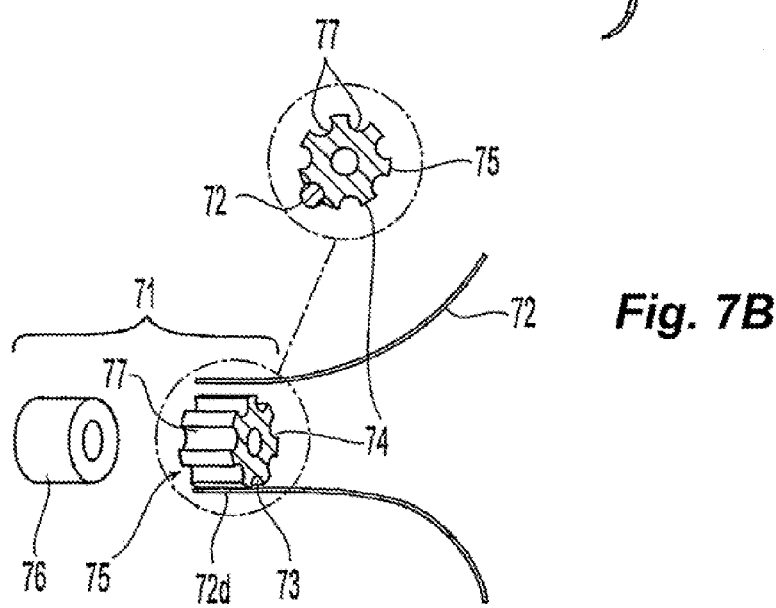
FIG. 7B is an exploded detail view of the filter positioning assembly illustrated in FIG. 7A.
Figures 7C, 7D:
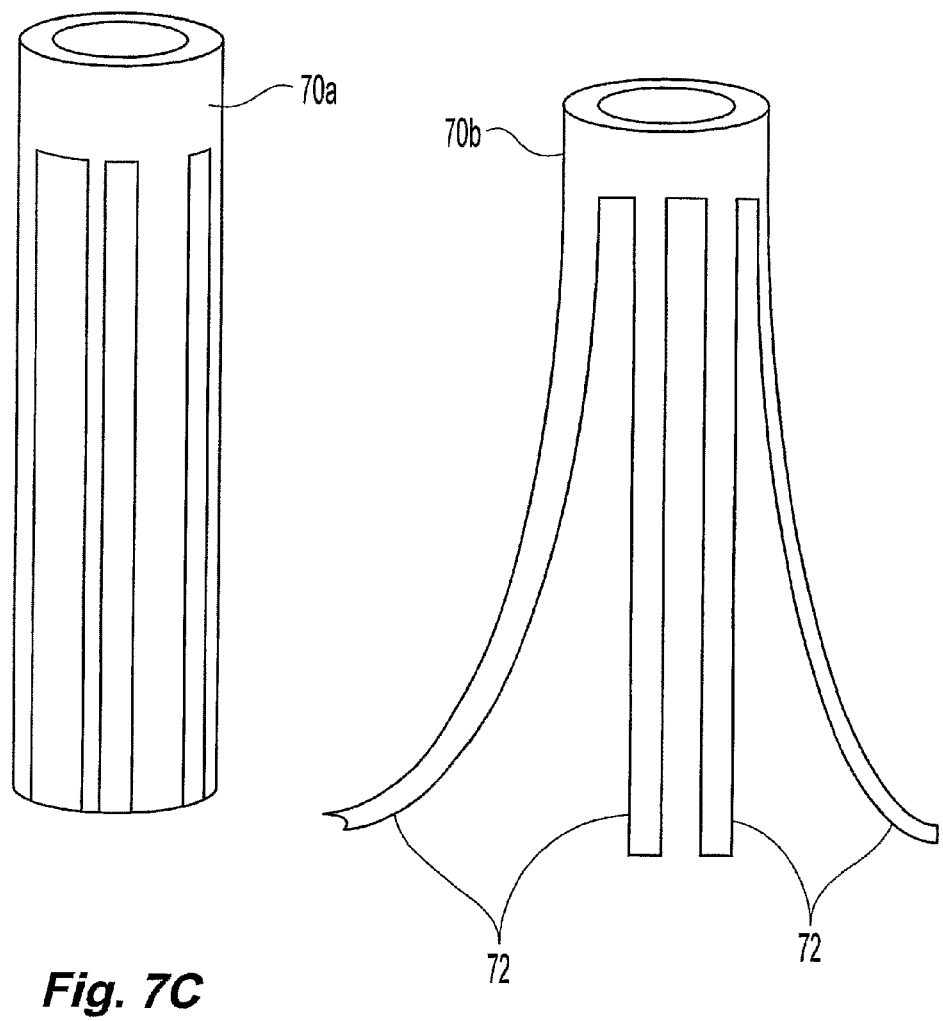
FIGS. 7C and 7D illustrate an alternative embodiment of the filter positioning assembly of FIGS. 7A and 7B.

An embodiment for assembling the filter positioning assembly 70 is illustrated in FIG. 7B. In this embodiment, the hub 71 is made up of a sleeve 76 that fits over an internal plug 75. The internal plug 75 may have grooves 77 sized to accommodate an attachment portion 72D of the positioner members 72 so that the sleeve fits close about the plug 75 and positioner member 72. With the sleeve in place, the assembly may be welded or brazed together into a rigid assembly.

Figure 8A:
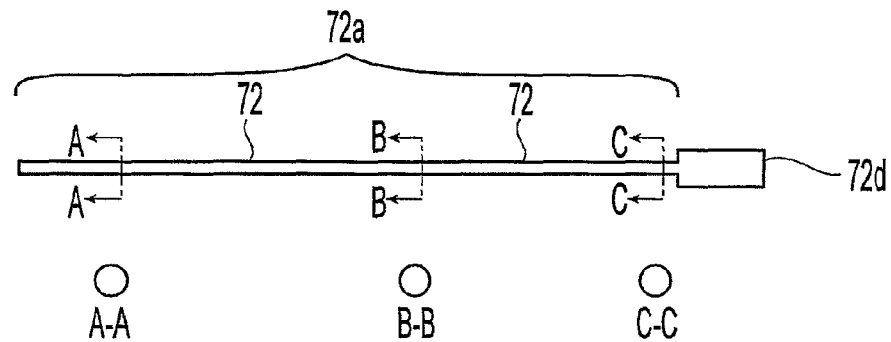
Figure 8B:
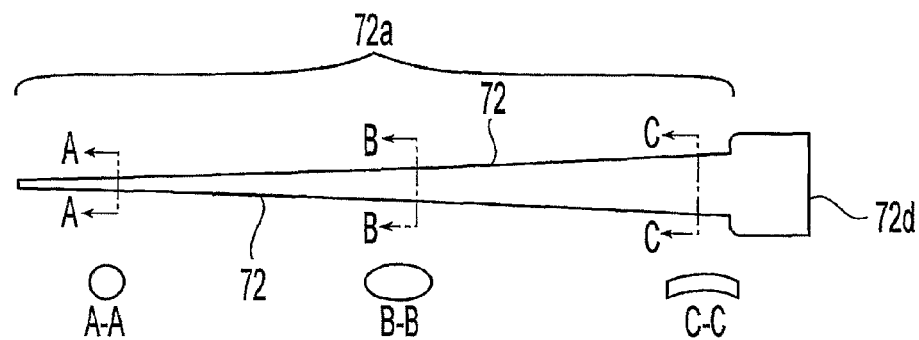
Figure 8C:
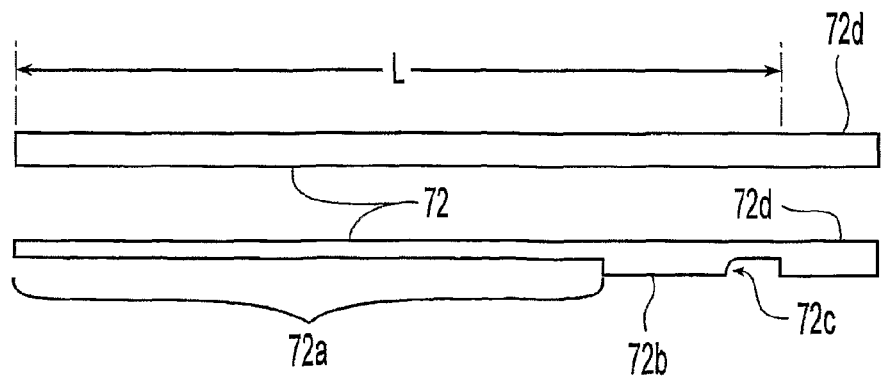

The positioner members 72 may be formed in a variety of shapes. Three nonlimiting example embodiments are illustrated in FIGS. 8A-8C. In the embodiment illustrated in FIG. 8A, the positioner members 72 may be a wire of relatively constant diameter, such as a circular, semicircular or elliptical cross section. While this embodiment features a constant cross section over its exposed length 72a, which is the majority of the member's length, it may also include a thicker portion 72d on its proximal end for added strength that is shaped to fit into a corresponding groove 77 on the plug 75 described above. In another embodiment illustrated in FIG. 8B, the positioner members 72 may feature a varied geometry along their exposed length 72a, which is the majority of the member's length, such as narrow and cylindrical at the distal end, and wide and rectangular or in the form of an arch at the proximal end. This embodiment may also have a thicker portion 72d on its proximal end for added strength that is shaped to fit into a corresponding groove 77 on the plug 75 described above. This embodiment may have design advantages because the tip portion, which presses against the vessel wall, can be thin and thus more flexible so as to avoid damaging the endothelial layer, while the proximal end can span greater width in order to better retain the anchor members until full deployment. In a third embodiment illustrated in FIG. 8C, the positioner members 72 may be thin strips, such as of a rectangular cross section over their exposed length 72a, which is the majority of the member's length. Like the other embodiments illustrated in FIGS. 8A and 8B, the positioner members 72 may have a thicker portion 72d on their proximal ends for added strength that is shaped to fit into a corresponding groove 77 on the plug 75 described above.

The positioner members 72 may also have cross sectional features provided to retain the anchor members 30 until release and provide additional volume for accommodating the hooks 40 of filter 1. For example, FIG. 8C illustrates a step portion 72b, which may be included in any of the other embodiments of the positioner members 72. When the positioner members 72 are coupled to the hub 71 to form the filter positioning assembly 70, the step portion 72b projects radially inward toward the centerline of the assembly. This creates a portion of the plurality of positioner members 72 having a narrower internal diameter for retaining anchor members 30 at that point. Such a narrow diameter on the interior of the positioner members 72 may tightly engage the anchor members so that longitudinal force necessary to push the filter 1 through the delivery catheter 16 can be transferred from the push rod assembly 60 to the filter anchor members 30 by the positioner members 72 at this point. A thinner cross section portion 72c may be provided adjacent to and on the proximal side of the narrower diameter formed by step portion 72b. This thinner cross section portion 72c can provide a larger volume in the assembly to accommodate the hooks 40 on the ends of the anchor members 30 in the assembled, pre-delivery configuration.

In addition to their cross sectional configuration, the positioner members 72 are characterized by their unconstrained shape over their length. In order to engage the blood vessel wall during delivery of the filter 1, the positioner members 72 bend radially away from the longitudinal axis of the filter positioning assembly 70. Thus, the positioner members 72 have a curved shaped and are fixed to the hub 71 so that their radiuses of curvature are outside the diameter of the hub 71. The curved shape may be formed before or after the positioner members 72 are coupled to the hub 71. When the positioner members 72 are made from a shape memory alloy, such as Nitinol, the curved configuration is set as the memory shape by annealing the member in the shape at high temperature, a step which may be completed either before or after the positioner members 72 are coupled to the hub 71. The shape memory alloy can further be defined as preferably having an austenite finish ($A_f$) temperature below body temperature. Additionally, the positioner member 72 can include an atraumatic tip such as, for example, a sphere, curved loop or a soft tip.

A number of positioner member 72 shape embodiments are possible consistent with the two functions performed by the structures. For example, FIG. 7A illustrates positioner members 72 with different radiuses of curvature over their length and which do not bend through a full 180 degrees. This embodiment places the positioner members 72 under less strain when they are collapsed around a filter 1 in the delivery configuration, illustrated in FIG. 11, and thus may be well suited for positioner members 72 made from spring materials such as stainless steel or Elgiloy®.

Another exemplary embodiment is illustrated in FIG. 9A, in which the positioner members 72 have a constant radius of curvature over their exposed length. In the embodiment illustrated in FIG. 9A, the positioner members 72 arch through a full semicircle (i.e., approximately 180 degrees), though they may curve through more or less than 180 degrees. In this embodiment, the positioner members 72 curve outward as they exit the delivery catheter 16, as illustrated in FIG. 9B, until they contact the vessel wall. This embodiment of the positioner members 72 has a number of advantages over the embodiment illustrated in FIG. 7A. For one, the wide angle between the positioner members 72 adjacent to the hub 71 may facilitate releasing the anchor members 30 by providing more clearance for the members to separate. For another, as the positioner members 72 advance out of the delivery catheter 16 (such as by the clinician pulling the catheter 16 in the proximal direction while holding the push rod 60 steady, as described more fully herein), the positioner members 72 will tend to bow in the distal direction as their tips are radially constrained by the blood vessel wall. This flexure may provide more space for releasing the anchor members 30 than may be the case for positioner members 72 that do not further flex away from the longitudinal axis, such as the embodiment illustrated in FIG. 7A.

Another example embodiment is illustrated in FIG. 9C, in which the positioner members 72 have an approximately constant radius of curvature over their entire length which is approximately equal to or longer than the circumference for that radius (i.e., $L \approx 2*\pi*radius$). In this embodiment, if the radius of curvature is set so that four times that radius plus the width of the hub 71 is approximately equal to the diameter of the blood vessel, the positioner members 72 will apply an approximately constant centering force against the vessel wall as the delivery catheter 16 is retreated. Referring to FIG. 9E, as the delivery catheter 16 is pulled back, the positioner members 72 will arch radially outward until the ends contact the vessel wall, providing a centering force on the hub 71. Then, as the delivery catheter 16 is further pulled back, the distal end of the positioner members 72 will arch back away from the vessel wall as illustrated in FIG. 9D so that the radial expansion of the positioner members 72 does not increase as the delivery catheter 16 is withdrawn. This curling over motion of the positioner members 72 continues with further retraction of the delivery catheter 16, as illustrated in FIG. 9C. Thus, in this embodiment, the maximum radial expansion of the positioner members 72 remains four times that radius plus the width of the hub 71. It should be noted that while the direction of curvature has been shown as counter-clockwise in FIGS. 9A-9E, it is also preferred that the direction of curvature originating from the catheter 16 is in a clockwise direction for FIGS. 9A-9E. Moreover, instead of a plurality of positioner members, a single helical coil can be used where the coil has an outside diameter at least as great as the blood vessel selected for implantation of a filter.

Since the embodiments illustrated in FIGS. 9A and 9C involve greater strain of the positioner members 72 to arrive at the pre-delivery, folded configuration illustrated in FIG. 11, these embodiments are preferably made from a super-elastic shape memory alloy, such as Nitinol. Using Nitinol, the shapes illustrated in FIGS. 9A and 9C can be set as the memory shape by annealing the positioner members 72 in these shapes at high temperature. The shape memory alloy can further be defined as preferably having an austenite finish ($A_f$) temperature below body temperature. After forming the members at high temperature, the members can be cooled below the martensitic-to-austenitic transition temperature so they become pliable for folding over the filter 1 into the configuration illustrated in FIG. 11. This alloy and method of assembly helps ensure that the positioner members 72 are elastically deformed during packaging.

Figure 10:
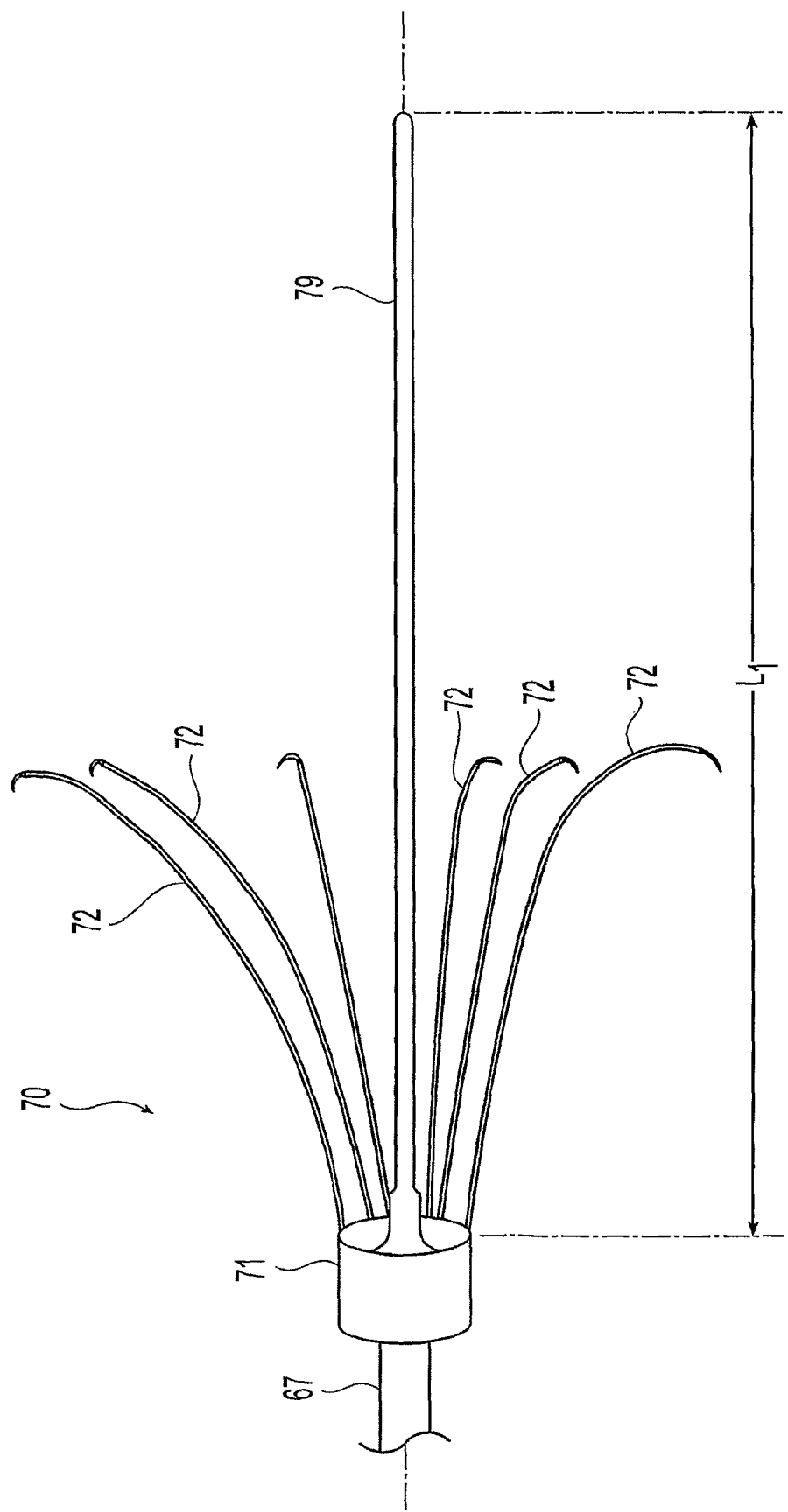
FIG. 10 is a detail view of another embodiment of a filter positioning assembly for use with a push rod assembly such as that shown in FIG. 6.

The filter positioning assembly 70 may include other features to facilitate delivery of a filter into a blood vessel. For example, FIG. 10 illustrates an embodiment that features an extension wire 79 projecting from the hub 71 along the longitudinal axis of the assembly for a length $L_3$. Referring to FIG. 2, length $L_3$ is the length of the anchor members 30 from the filter hub 2. Thus, in this embodiment of the filter positioning assembly 70, the extension wire 79 will reach up to the base of the filter hub 2. Using a relatively stiff material for the extension wire 79, the member can transfer the pushing force directly from the push rod 60 to the filter hub 2. This embodiment reduces the longitudinal force of pushing the filter 1 through the delivery catheter 16 that must be resisted by the anchor members 30. While the extension wire 79 is shown for pushing the filter during deployment, an alternative embodiment can be provided where the positioner members 72 can be used to push on the filter hub 2 while the anchor members 30 are restrained between a splined hub and the catheter. Details of the splined hub and catheter to restrain the anchor members of the filter are shown and described in PCT International Application No. PCT/US06/17890, entitled "Embolus Blood Clot Filter and Delivery System," filed on May 9, 2006, which is hereby incorporated by reference in its entirety.

From the foregoing, it can be seen that the various embodiments of the positioner members 72 described herein and illustrated in the figures provide means for aligning a blood filter with a blood vessel centerline and retaining anchor members of the filter until the alignment has been accomplished. The positioner members 72 also provide means for releasing anchor members 30 only after the blood filter has been aligned with the blood vessel centerline. Further, the push rod assembly provides means for pushing a blood filter through a delivery catheter and deploying the filter in the blood vessel so the filter is aligned with the blood vessel's center.

Preferably, during manufacturing, the filter positioning assembly 70 is fitted over the filter 1 and positioned within a storage tube 15. In the assembled configuration, illustrated in FIGS. 11 and 12, positioner members 72 will be constrained by the walls of the storage tube 15 or catheter 16 so that they lie approximately parallel to the longitudinal axis, fitting tightly over the anchor members to present a narrow cross section assembly that will fit within a delivery catheter. The combined filter positioning assembly 70 and filter 1 may be kept in a storage tube 15 which preferably has approximately the same internal diameter as the delivery catheter and is configured to be coupled to the catheter by a clinician.

FIG. 12 illustrates an example of a suitable storage tube 15 containing a combined filter positioning assembly 70 and filter 1. The inner diameter of the storage tube 15 resists radial expansion of the filter's locator members 20 and the positioner members 72, keeping them locked over the anchor members 30. In the embodiment illustrated in FIG. 12, the push rod terminal portion 67 is coupled to the hub 71 and included within and/or extends from an end of the storage tube 15. Alternative embodiments for connecting the terminal portion 67 to the hub 71 just before use are described herein with respect to FIGS. 14A-C. In an embodiment, the terminal portion 67 is coupled to the push rod assembly 60 during storage, so the filter 1, storage tube 15 and push rod assembly 60 are packaged and stored as complete unit. In another embodiment, the terminal portion 67 includes a coupling mechanism that allows the clinician to connect the terminal portion 67 to the rest of the push rod assembly 60 at the time of use. Any number of well-known mechanisms for connecting rods together (e.g., threaded connections, bayonet fit, groove-and-detent fit, etc.) may be used for such a connection.

Figure 29:
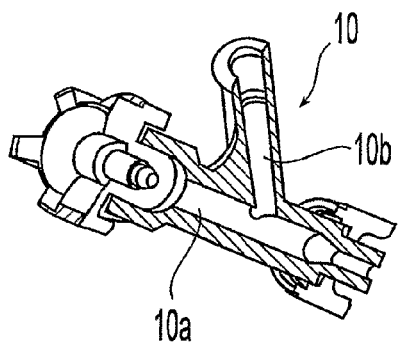
FIG. 29 is a detail view of an adapter portion of the filter delivery system of FIG. 21.
Figure 30:
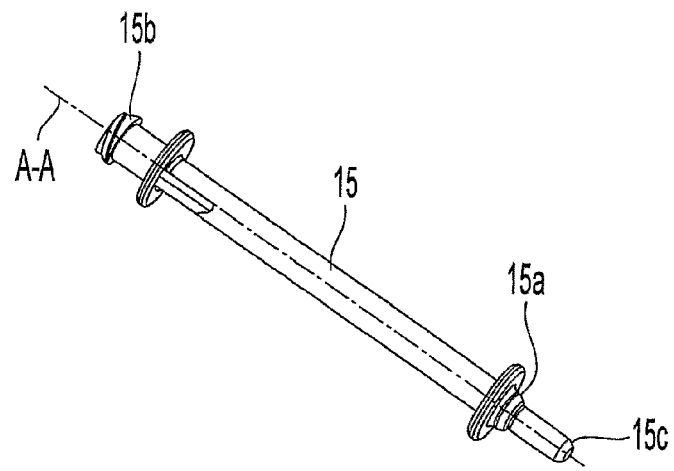
FIG. 30 is a perspective view of a filter storage tube portion of the filter delivery system of FIG. 21.

Referring to FIGS. 12 and 30, the storage tube 15 for various blood filters may be provided with a suitable fitting (e.g., threaded, snap or luer fitting) at both ends for connection to other elements of a delivery system, such as described in more detail herein. In an embodiment, the storage tube 15 has a threaded fitting 15b at one end to connect with a Touhy-Borst Adapter 10, such as is illustrated in FIG. 29, and a snap fitting 15a at the other end to connect with the delivery catheter 16, as well as a taper section 15c for insertion into an elastomeric seal on the catheter. Alternatively, one end can be provided with a snap-fitting and the other end can be provided with a threaded fitting. The storage tube 15 can be formed from any of a number of suitable polymers and, preferably, polycarbonate.

To shorten the as-assembled filter positioning assembly 70 and filter 1 combination so that it can be enclosed and sealed within a relatively short storage tube 15, a connectable fitting may be provided between the hub 71 and the push rod terminal portion 67. Such a connectable fitting may be any known mechanical joining connection. Three nonlimiting examples of known connections are illustrated in FIGS. 14A-C. For example, as illustrated in FIG. 14A, the terminal portion 67 may be fitted with tabs 81a that match corresponding grooves within a bore 81b in the hub 71 to provide a bayonet connection 81. In another example, illustrated in FIG. 14B, the end of the terminal portion 67 may be threaded 82a to match corresponding threads in a bore 82b within the hub 71 to provide a threaded connection 82. In a third example, illustrated in FIG. 14C, spring tabs 83a may be fixed to a nib end 83b of the terminal portion 67 which will slip into a bore 83c in the hub 71 and latch into an internal ridge 83d to provide a snap connection 83. By using a connectable fitting, the filter positioning assembly 70 and filter 1 may be stored in a relatively short sterilized and sealed storage tube 15 that can be maintained in a conventional medicinal refrigerator (e.g., in order to maintain Nitinol elements below the martensitic-to-austenitic transition temperature). Then, at the time of use, an end of the storage tube 15 may be opened and the filter positioning assembly 70 connected to the terminal portion 67 of the push rod assembly 60 by the clinician.

Figure 13A:
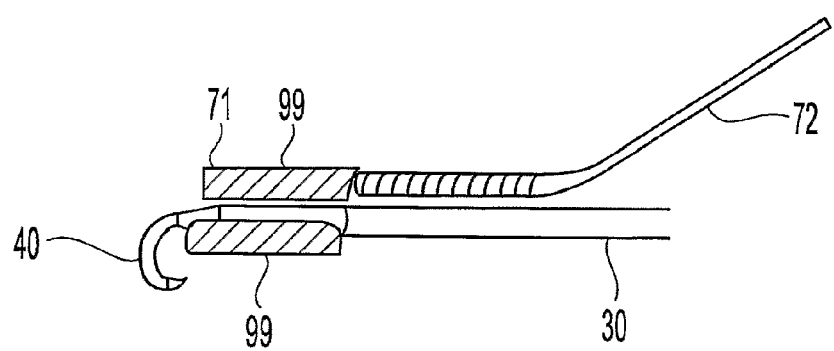
FIG. 13A is a side view of an embodiment of the filter positioning assembly including a spline near its base to contain the filter anchor members.
Figure 13B:
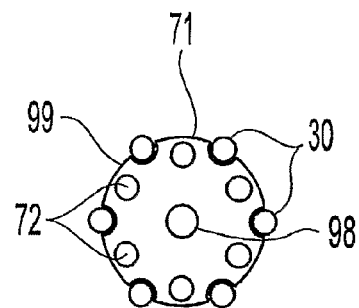
FIG. 13B is a cross sectional view of the filter positioning assembly shown in FIG. 13A.

FIGS. 15-20 illustrate the structure and functioning of the various embodiments delivering a filter into a blood vessel. In operation and storage, the positioner members 72 remain tightly linked over the anchor members 30, held in place by the walls of the storage tube 15 or delivery catheter 16 until they are fully clear of the catheter. To help restrain the filter anchor members 30 prior to deployment, the filter positioning assembly 70 may include a spline 99 such as that illustrated in FIGS. 13A and 13B. The spline 99, which is preferably situated at or near and more preferably formed in the positioning assembly hub 71, secures the filter anchor members 30 generally about the hub 71 and thereby prevents the filter hooks 40 from becoming entangled before deployment. The positioner members 72 may be integral with the spline 99 and the spline may include a central lumen 98, as illustrated in FIG. 13B.

Figure 15:
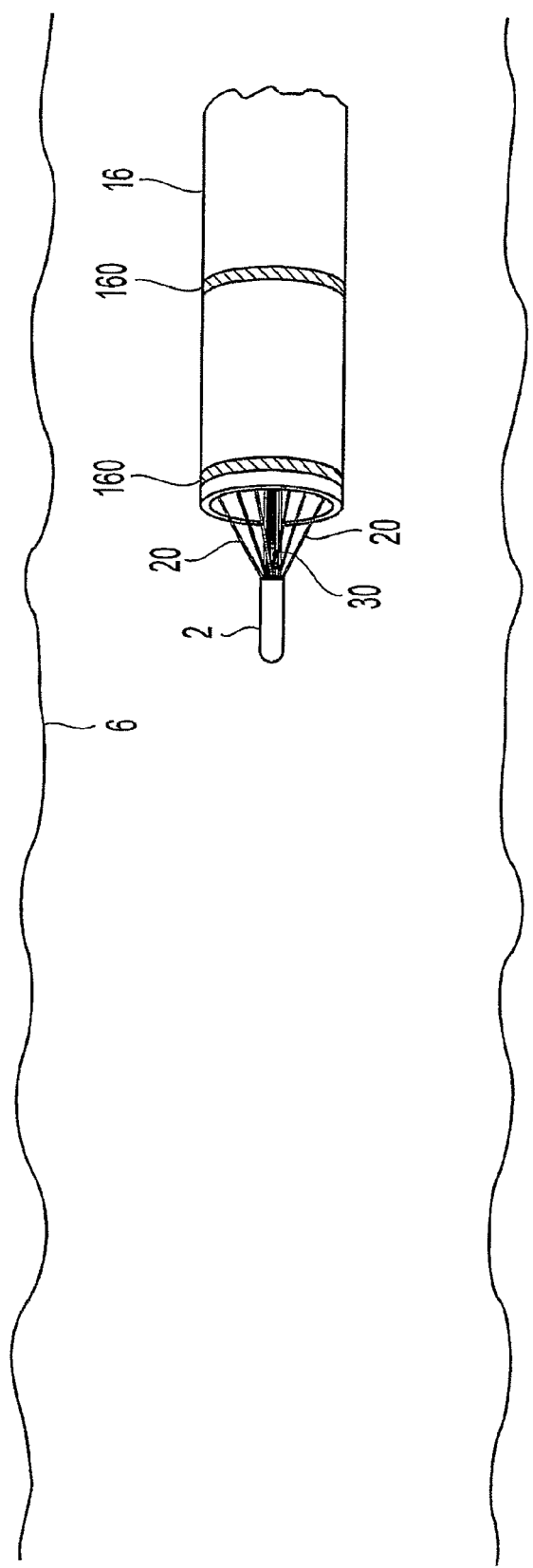
FIGS. 15-20 illustrate steps in the delivery of a blood filter into a blood vessel.

In use, a clinician will typically position the delivery catheter 16 to a position in a blood vessel 6 where filter placement is desired. To aid the clinician in this step, the delivery catheter 16 may have one or more radio-opaque markers 160 near its distal end and at various lengths, which can be imaged using fluoroscopy. With the catheter so positioned, the filter positioning assembly 70 and filter 1 may be loaded into the proximal end of the delivery catheter 16 and advanced by pushing on the handle 61 of the push rod assembly 60 while holding the delivery catheter 16 in a fixed position. When the filter 1 is near or just beyond the end of the catheter 16, as illustrated in FIG. 15, the hub 2 is at the position where filter placement is desired. To help confirm the position of the filter 1, the hub 2 may include a radio-opaque marker that can be imaged by fluoroscopy equipment. At this point, the filter locator members 20 remain retained by the catheter walls.

Figure 16:
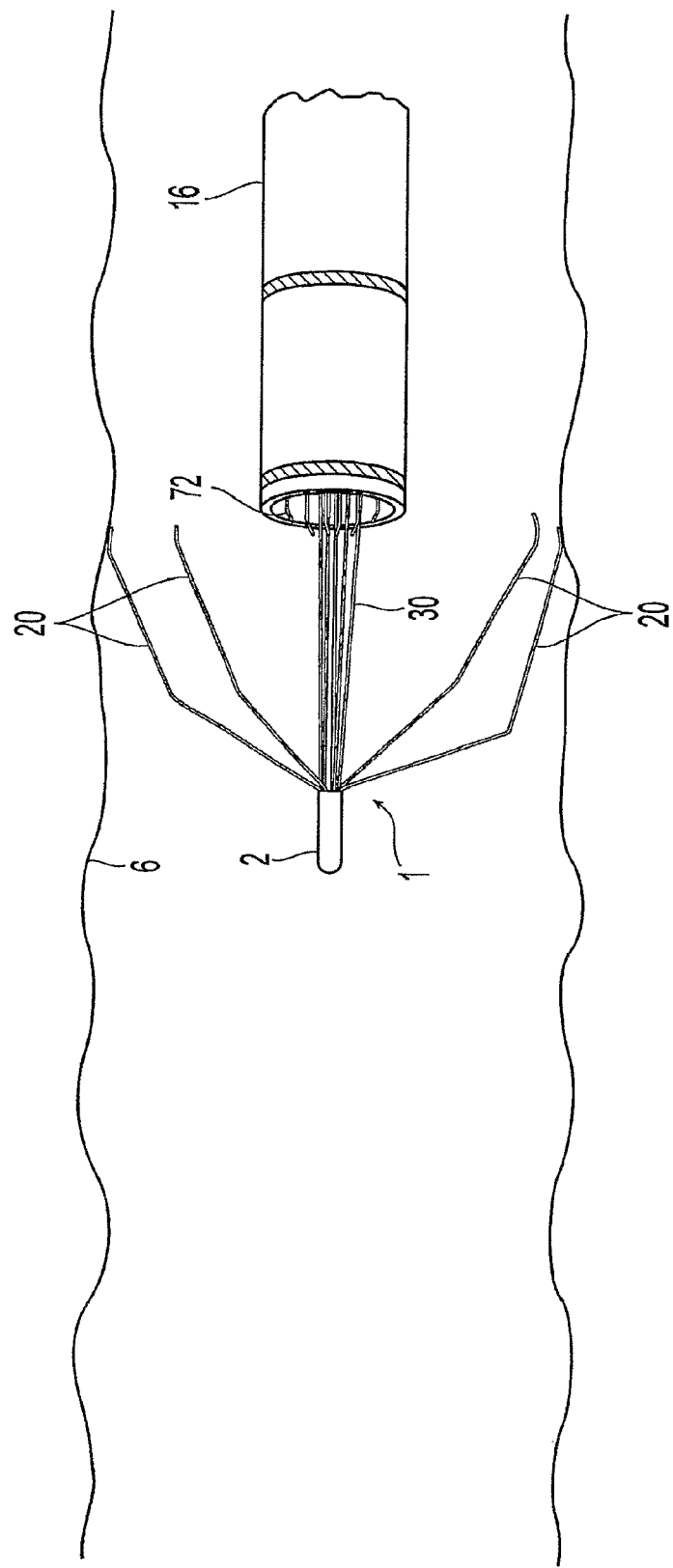

To deliver the filter, the clinician now extends the filter 1 and positioner members 72 beyond the end of the delivery catheter 16. This may be done by either advancing the push rod assembly in the distal direction while holding the catheter in a fixed position or, preferably, retracting the delivery catheter 16 in the proximal (withdrawal) direction while holding the push rod assembly 60 in a fixed position. The push rod assembly is advanced or the catheter 16 is retracted until the filter locator member tips clear the end of the catheter as illustrated in FIG. 16. Once free of the catheter, the locator members deploy so that their ends press against the vessel wall 6, thereby centering the filter hub 2 near the vessel centerline. At this point, the positioner members 72 retain the anchor members 30, preventing them from deploying.

Figure 17:
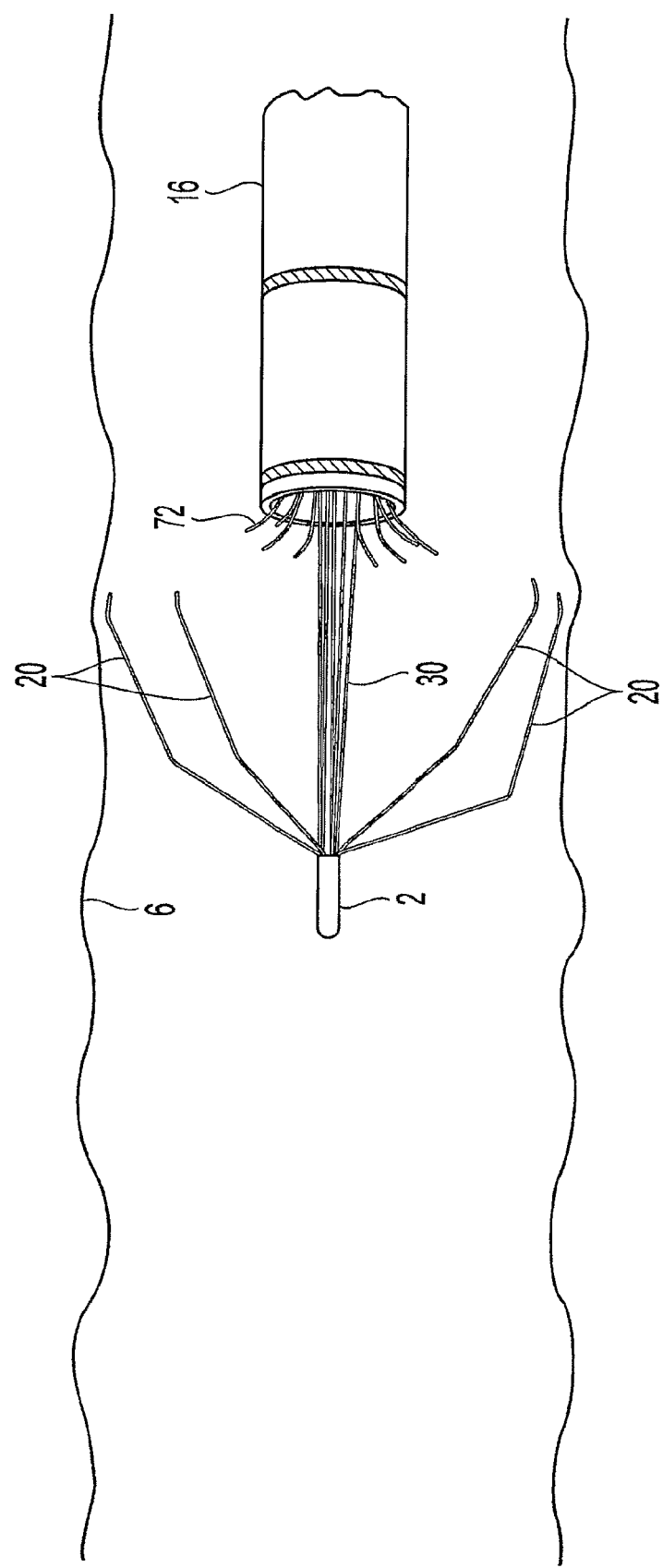
Figure 19:
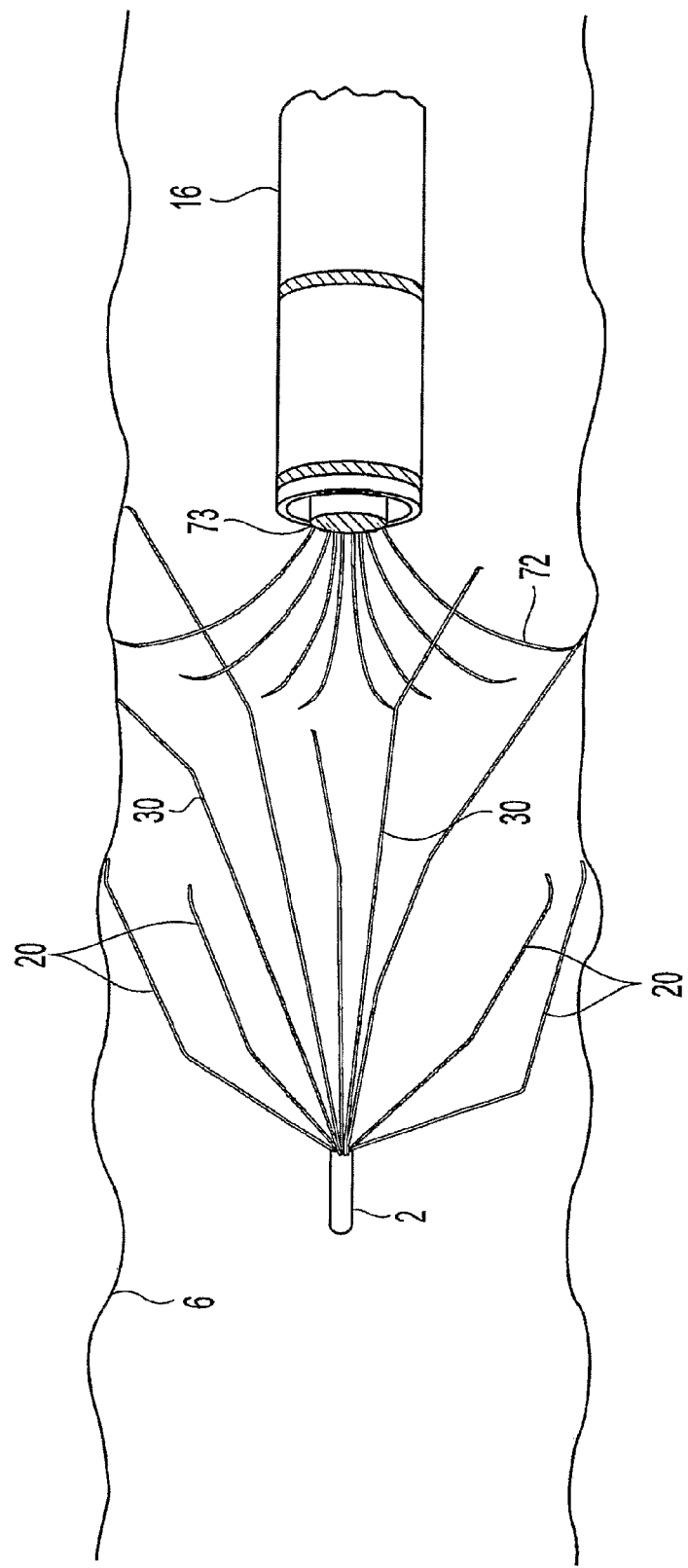
Figure 20:
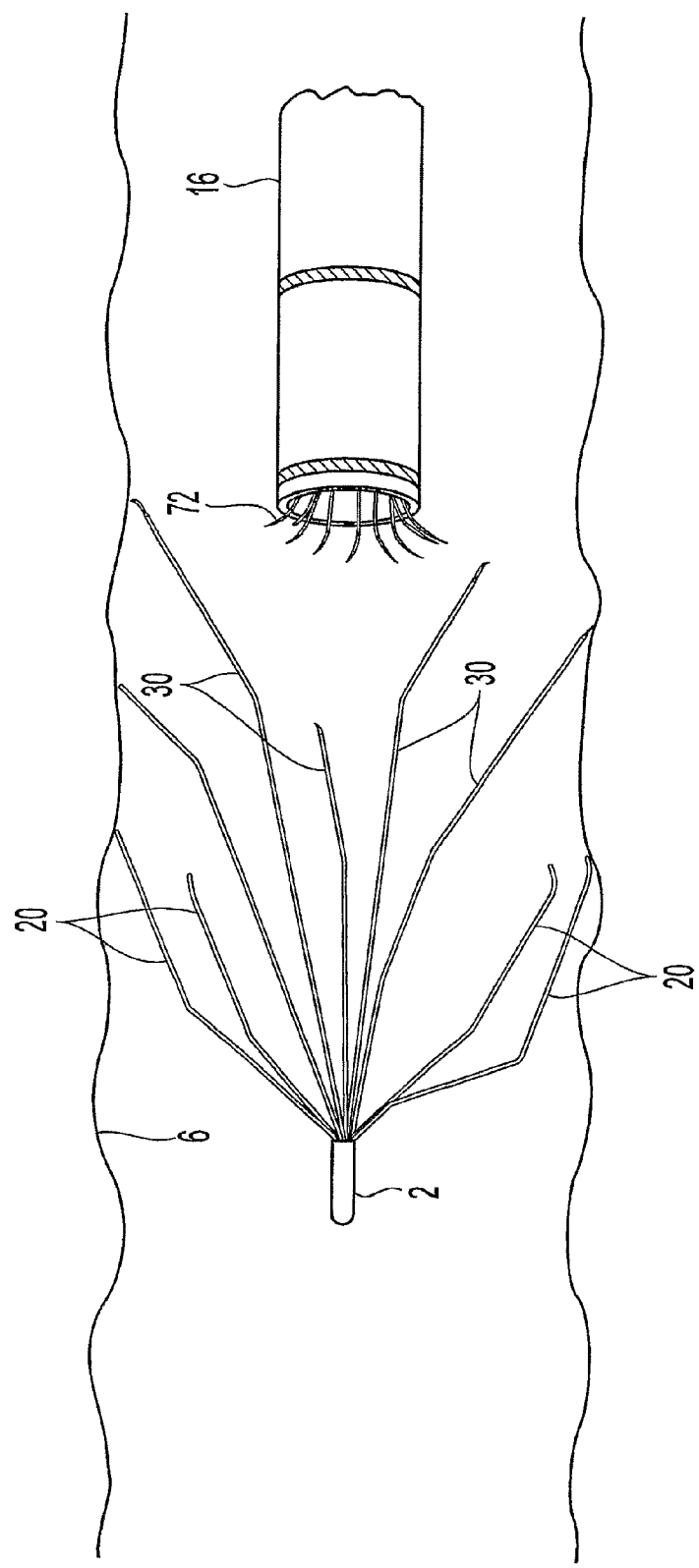

As the push rod assembly is further advanced or the delivery catheter 16 is further retracted, the positioner members 72 begin to be uncovered, which allows the tips of the positioner members 72 to flex radially outward seeking their memory shape, as illustrated in FIG. 17. Once the push rod assembly has been sufficiently advanced or the delivery catheter 16 has been sufficiently retracted, the ends of the positioner members 72 contact and press against the blood vessel wall 6 as illustrated in FIG. 18. The forces applied by the positioner members 72, being equal in all directions, center the distal end of the delivery catheter 16 within the blood vessel 6. The combination of the centering action of the locator members 20 acting on the filter hub 2 and the positioner members 72 acting on the catheter 16 and hook-ends of the anchor members 30 aligns the filter 1 approximately parallel with the blood vessel's centerline. At this point, the positioner members 72 still retain the anchor members 30, preventing them from deploying until the aligning movements are completed. Then, when the delivery catheter 16 is retracted a little further, the positioner members 72 are fully released which by flexing away from the filter 1, release the anchor members 30, as illustrated in FIG. 19. This allows the anchor members 30 to spring radially outward toward their memory shape, pressing the hooks 40 into the vessel wall 6, thereby anchoring the filter 1 in place. Finally, the clinician pulls the push rod assembly 60 in a proximal direction while holding the delivery catheter 16 in a fixed position to pull the positioner members 72 back into the catheter 16, as illustrated in FIG. 20. Once the positioner members 72 are securely within the delivery catheter 16, the assembly can be removed from the patient's body.

An example of a suitable method for joining filter 1 with the filter positioning assembly 70 and loading the combination in the storage tube 15 is now described. The method comprises several steps. First, the components are chilled below their martensitic-to-austenitic transition temperature so that the positioner members 72 and filter members, which are preferably made from a shape memory alloy like Nitinol, are flexible. At this stage, the positioner members 72 are compressed, such as by slipping a plastic tube over the members, and the filter positioning assembly 70 are passed through the storage tube so they are accessible on the other side, after which the plastic tube is removed.

Second, the filter is folded to its narrow profile configuration illustrated in FIG. 2. This may be accomplished by slipping a plastic tube over the filter hub 2 and folding the locator members 20 and then the anchor members 30 toward the longitudinal axis while advancing the tube over the filter 1. The tube used for compression must only be advanced far enough to collapse both the locator members and the anchor members. The tube need not be advanced all the way to the hooks 40. In this stage, the compressed filter and surrounding plastic tube are positioned so the anchor hooks rest against the hub 71 and are centered among the positioner members 72. The anchor members 30 should be aligned with the positioner members 72.

Third, the storage tube 15 is moved slowly toward the filter and over the positioner members 72. The walls of the storage tube force the positioner members 72 to collapse toward the longitudinal access and close over the anchor members 30. As the positioner members 72 collapse upon the anchor members, the plastic tube used to compress the filter is retracted so the tube does not become bound between positioner members 72 and anchor members 30. This process continues until the positioner members 72 are encompassed by the storage tube 15. At this stage, the positioner members 72 will lie generally parallel to the longitudinal axis and fully encircle the anchor members 30.

Finally, the storage tube 15 is advanced over the rest of the filter with the plastic tube in place to hold the locator members in their collapsed configuration. Once the entire filter 1 is within the storage tube 15, the plastic tube is withdrawn and the storage tube is sealed. To facilitate this method of assembly, the plastic tube may be clear and thin walled, with an external diameter just smaller than the inside diameter of the storage tube. This assembly process is performed prior to shipment to the user or medical practitioner. Other assembly methods may be used, and assembly may be facilitated by using other jigs or assembly tools to assemble the filter members within positioner members 72 for loading into the storage tube 15.

To complete assembly, the storage tube 15 may be sealed on both ends to prevent contamination from entering, and the entire assembly of the push rod assembly 60, filter 1 and storage tube 15 are sealed in sterile packaging. To avoid kinking of the push rod assembly 60 or lateral forces on the storage tube 15, the entire assembly may be packed in a linear manner within a foam form and hard outer package, such as cardboard or plastic.

The various embodiments of the push rod assembly 60 will typically be used in combination with other filter delivery system components, particularly a catheter 16 that supports delivery of a filter into a blood vessel. A nonlimiting example embodiment of a filter delivery system suitable for use with the foregoing embodiments of the push rod assembly 60 follows with reference to FIGS. 21-30.

Figure 21:
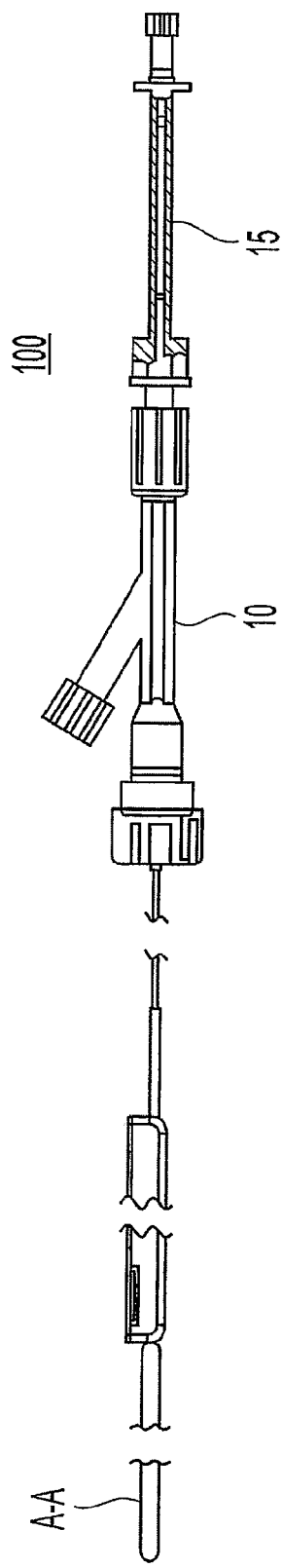
FIG. 21 is an assembly view of an example embodiment of a filter delivery system suitable for use with various embodiments of the present invention.

In overview, the blood filter delivery system 100 includes a storage tube 15 containing the filter 1, a catheter introducer 16 ("catheter introducer" here refers to a particular embodiment of the delivery catheter 16 so the same designation reference is used) and the push rod assembly 60 for pushing the filter 1 from the storage tube 15, through the catheter introducer 16 and then into the blood vessel, as well as supporting adapters illustrated in FIG. 21. The blood filter delivery system 100 for a blood filter device extends along a longitudinal axis A-A. Components of the system include an adapter 10, such as the Touhy-Borst Adapter shown in FIG. 29, a filter storage tube 15 (FIG. 12 and 30) that can be coupled to the Touhy-Borst Adapter 10 with a filter 1 stored in the storage tube 15 along with one of the various embodiments of the filter positioning assembly 70 that can be used to deploy the filter 1 in a blood vessel of a patient. Other components that may be used with the system include a catheter introducer 16, shown in FIG. 22, and a catheter dilator 18, shown in FIG. 25. Each system component is described in further detail below.

Figure 22:
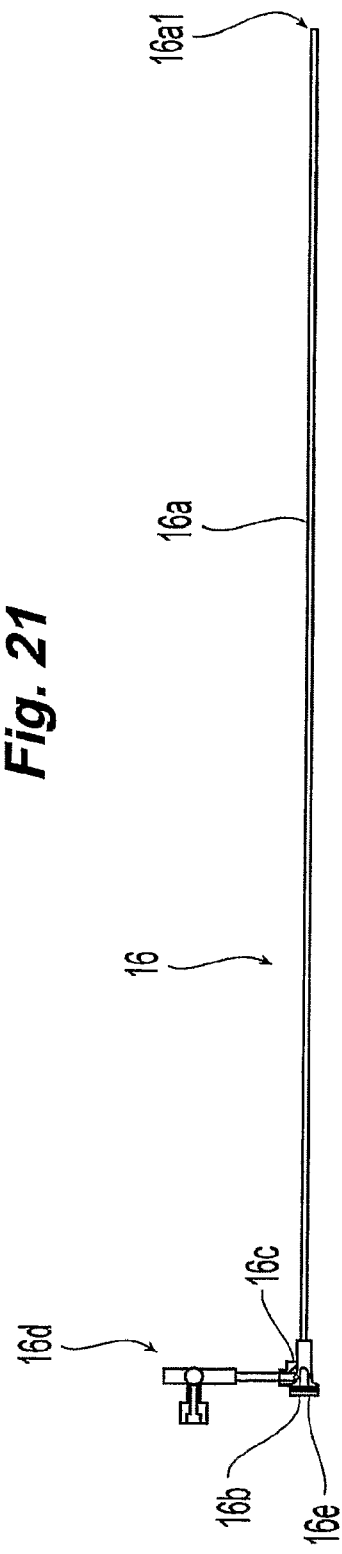
FIG. 22 is a side sectional view of a delivery catheter suitable for use with various embodiments of the present invention.
Figure 24:
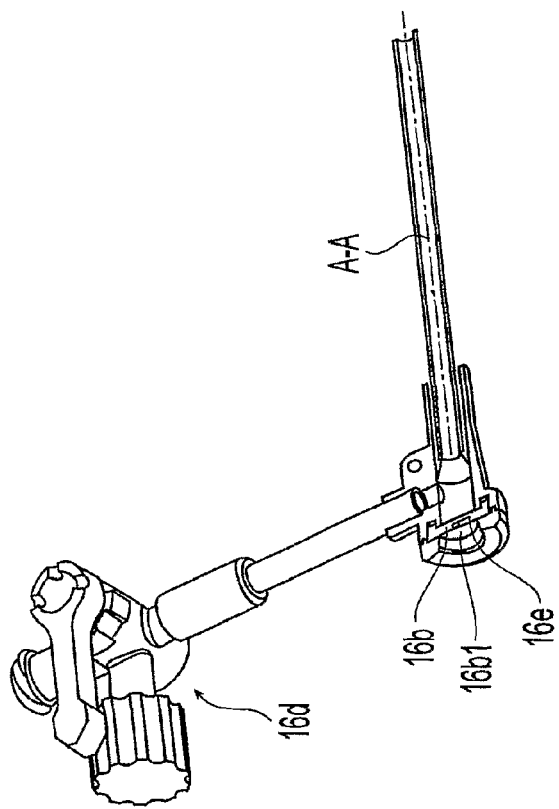
FIG. 24 is a perspective view of portions of the delivery catheter of FIG. 22.
Figure 23:
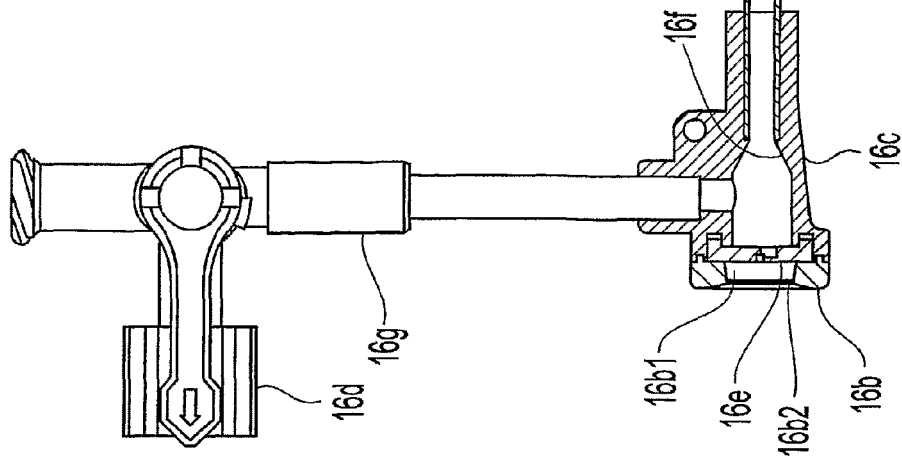
FIG. 23 is a detail sectional view of portions of the delivery catheter of FIG. 22.

Referring to FIGS. 22, 23, and 24, a catheter introducer 16 includes an elongated generally tubular member, referred to herein as the introducer sheath 16a coupled to a coupling port 16b via an introducer body 16c, which may be provided with a fluid valve 16d. The elongated introducer sheath member 16a is coupled to the introducer body 16c by suitable coupling techniques, such as, but not limited to, threading, bonding, welding, swaging or adhesives. The introducer body 16c can be provided with an internal taper portion 16f that allows for insertion of the external taper portion 15c of the storage tube 15 (FIG. 30) and to allow for insertion of the filter hub 2 without interference by misalignment of the storage tube 15 to the introducer sheath 16a during insertion of the storage tube 15 into the introducer 16. Each of the respective taper portions 16f and 15c is preferably provided with a taper angle of about 10 degrees to about 45 degrees with respect to the longitudinal axis A-A.

In various embodiments, the introducer sheath member 16a may be formed from a range of biocompatible flexible materials, such as polyurethane, polyethylene, polyamide, polyether block amide (PEBA), nylon, and combinations thereof, preferably from a combination of PEBA 70D with PEBA 55D proximate the tip 16a1. The introducer sheath member 16a may be connected to the introducer body 16c by a bio-compatible adhesive, e.g., cyanoacrylates. In an embodiment, the distal tip 16a1 of the introducer sheath member 16a can be provided with a suitable radio-opaque marker 160, or include radio-opaque marker substances within the material of the introducer tip 16a1. Preferably, a tantalum radio-opaque marker is formed on or near the tip 16a1 of the introducer sheath 16a.

In a preferred embodiment, the introducer sheath 16a has an outside diameter of less than about No. 10 French and an inside diameter of less than about No. 9 French and more preferably, an outside diameter of about No. 9 French or less and an inside diameter of about No. 7 French or less, depending upon limits imposed by the diameter of the blood filter in the pre-deployed (i.e., folded) configuration.

The introducer body 16c may be provided with a coupling port 16b, which may include a fluid seal 16e interposed between the port opening 16b1 coupled to the introducer sheath member 16a. The fluid seal 16e may be any suitable seal, such as but not limited to, a membrane or a flexible arcuate sectioned seal disposed about a central opening Preferably, the seal 16e is an elastic membrane made of a suitable biocompatible elastomer, e.g., silicone, with the arcuate sectioned seal disposed about a generally central opening 16b1 for insertion of the dilator 18 or the filter storage tube 15. The introducer body 16c may be coupled to a fluid valve 16d via a polymeric (e.g., PVC) tubing 16g to allow for a suitable fluid (e.g., saline or a bio-active agent including drugs) to be introduced into the introducer sheath 16a or to drain fluid from the introducer sheath 16a. Preferably, the valve 16d and introducer body 16c are made of polycarbonate, polyethylene, polyurethane, polyamide or PEBA. The coupling port 16b may be provided with a circumferential edge that may be configured to act in a snap-lock arrangement with a complementary boss portion 18f of the dilator body 18a to attach and retain the dilator body 18a to the introducer body 16c. That is, the coupling port 16b includes the introducer body 16c that has the port opening 16b1, which has a seal 16e occluding the opening 16b1, and the introducer body 16c has an edge 16b2 disposed about the opening 16b1 so as to allow the introducer body 16c to be securable to a projection 15a formed on one end of the storage tube 15 via a sudden sharp engagement. The projection 15a of the storage tube 15 may include a curved surface disposed circumferentially about the longitudinal axis A-A.

The use of complementary snap-fittings for the storage tube 15 and introducer body 16c along with the internal and external tapers 16f and 15c are believed to allow for precise coupling of these two components without having to align the storage tube with the body 16c and threading the two components together, which under some circumstances could result in cross-threading or interference with the tip of the filter 1 into the introducer sheath 16a.

Alternative embodiments of the introducer 16 may provide additional capabilities for delivering and inspecting a blood filter. In one embodiment, an ultrasound imaging transducer is included in or near the distal end 16a1 positioned to be capable of imaging the deploying and deployed filter using ultrasound-imaging technology. An example of a suitable ultrasound transducer technology is disclosed in U.S. Pat. No. 5,325,860, which is incorporated by reference herein in its entirety. By incorporating an ultrasound imager within the introducer 16, a clinician can visually confirm the placement, deployment and emplacement of the filter 1 before removing the introducer 16 while minimizing the use of fluoroscopy. In an alternative embodiment, an ultrasound imaging transducer may be passed through the introducer 16 after the push rod assembly 60 has been withdrawn following delivery of the filter 1. This embodiment allows the clinician to image the implanted filter before removing the introducer 16 from the vicinity of the filter.

In another alternative embodiment, a fiber optic imager or borescope is included within the introducer sheath 16A to provide the clinician with a visual image of the deploying and deployed filter. A small lens on the distal end of an optical fiber or bundle of optical fibers conveys an image to a small video camera on the proximal end. Illumination may be provided to the point of inspection by another or the same optical fiber. Such a fiber optic imager may be built into the wall of the introducer sheath 16a or be passed through the introducer sheath 16a after the push rod 60 has been withdrawn following delivery of the filter. To aid in visualizing the implanted filter, saline solution may be introduced in the introducer to displace blood in the volume being imaged. Similar to an ultrasound imager, use of a fiber optic imager would permit a clinician to confirm the proper placement, deployment and emplacement of the filter before removing the introducer 16 while minimizing the use of fluoroscopy.

The use of ultrasound or visual inspection of the deployed filter while the introducer 16 is in position near the filter may allow the clinician to remove an improperly deployed or located filter and replace it with another without requiring a separate procedure and before endothelial overgrowth of the filter hooks takes place. In this manner, if the filter is improperly deployed and requires removal, the introducer 16 is already adjacent to the filter and ready to be used in the removal procedure.

Figure 28:
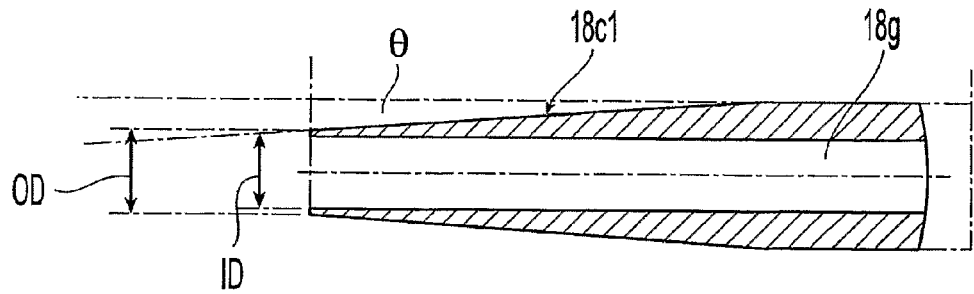

A catheter dilator 18 is preferably used in conjunction with the introducer 16. Referring to FIGS. 25-27, the dilator 18 includes a dilator body 18a coupled to a dilator tube 18b. The dilator body 18a is provided with a threaded fitting 18f at the proximal end to connect to a suitable fluid valve, e.g., the Touhy-Borst Adapter 10 (FIG. 29) so that fluids can be injected into the dilator fluid passage 18g (FIG. 28). A number of fluids may be injected during an operation, including dye marker for enabling fluoroscopic imaging of the introducer 16 within the patient, saline to flush body fluids from and provide lubrication within the introducer 16 and, in some embodiments, cooled saline to maintain temperatures of the push rod and/or the filter below their martensitic-to-austenitic transition temperature. The dilator body 18a is coupled to a dilator tube 18b that extends through and provides a longitudinal passage 18g of approximately 26 inches (approximately 661 mm) from the dilator body 18a to the distal dilator end 18c. At the distal dilator end 18c, the dilator tube 18b may be provided with a generally truncated conic tip defined by the outer surface of the distal end 18c. The conic tip 18c1 can be defined by a conic outer surface that extends at a conic angle θ of about 4 degrees with respect to the longitudinal axis with an inside diameter ID of about 0.041 inches and an outside diameter OD of about 0.084 inches.

A plurality of fluid communicating ports 18d may be provided through the wall of the dilator tube 18b in a generally spiral configuration to allow for injection of contrasting dye. Each fluid communicating port 18d can be of a suitable configuration including, but not limited to, circular, square, or diamond. Preferably, as shown in FIG. 27, six circular communicating ports 18d1, 18d2, 18d3, 18d4, 18d5, and 18d6 are provided with an opening diameter of about 0.037 inches. Each port is preferably spaced equidistantly from the adjacent port over a distance d of about 0.16 inches along the longitudinal axis A-A and angularly disposed about the longitudinal axis A-A over an interval of 60 degrees with respect to each adjacent port.

One or more radio-opaque marker bands 18e may be coupled to the dilator body 18a by a suitable technique, such as, but not limited to, forming a radio-opaque material integrally with the dilator tube 18b or mounting a separate radio-opaque material onto or inside the dilator tube 18b. Preferably, two radio-opaque markers 18e are swaged onto the dilator tube 18b near the distal end 18c, with a first marker 18e1 located approximately 1.1 inches (approximately 28 mm) from the tip 18c and a second marker 18e2 located at approximately 1.1 inches (approximately 28 mm) from the first marker 18e1. In an embodiment, the ports 18d1-d6 are arranged in a spiral configuration between two radio-opaque marker bands.

The dilator tube 18d may be formed from a variety of biocompatible flexible materials, such as polyurethane, polyethylene, polyamide, polyether block amide (PEBA), nylon, and combinations thereof, preferably from a HDPE/LLDPE blend of polymer and 18-20% of barium sulfate by weight, with the barium sulfate providing the radio-opaque functionality.

When assembled, the dilator tube 18b slides inside the introducer sheath 16a such that the dilator tube tip 18c1 is close to the introducer tip 16a1. The introducer 16 and catheter dilator 18 may be packaged separately, such as in separate sterilized packages, so they can be unsealed and assembled by the clinician at the time of the procedure. Alternatively, the catheter dilator 18 may be inserted into the introducer 16 at the manufacturer and sealed together in a sterile package, such that the clinician can unpack and use the two components as a unit.

Referring to FIG. 29, the Touhy-Borst Adapter 10 may be provided with at least two passages. A first passage 10a allows for movements of the push rod assembly 60. A second passage 10b allows for flow of saline into the introducer 16 to increase lubricity between the push rod assembly 60 and the introducer 16 as the elongated push rod assembly 60 is moved along longitudinal axis A-A through the second passage 10b and the passage of the introducer 16. The saline solution also may be chilled before introduction into the Touhy-Borst Adapter 10 in order to maintain temperatures of the push rod and/or the filter below their martensitic-to-austenitic transition temperature.

Referring to FIG. 30, the storage tube 15 is provided with a suitable fitting (e.g., threaded, snap or luer fitting) at both ends. In an embodiment, the storage tube 15 has a threaded fitting 15b at one end to connect with the Touhy-Borst Adapter 10 and a snap fitting 15a at the other end to connect with the introducer 16, as well as a taper section 15c for insertion into the preferably triple arcuate sectioned elastomeric seal 16e.

The example filter delivery system may be used as follows for implanting a blood filter into a host. At the start, a suitable femoral venous vessel site in the host may be selected. Typically, this is the femoral vein on either the left or right side, depending upon the patient's size or anatomy, the clinician's preference and/or the location of a venous thrombosis. The site may be nicked with a blade and the vein punctured with a suitable entry needle, such as an 18-gauge needle, or trocar. A suitable guide wire, such as a J-tipped guide wire, is inserted into the needle and advanced into a distal vena cava or iliac vessel where a filter is to be delivered. Once the guide wire is in position, the entry needle is removed from the patient and slipped off the proximal end of the guide wire. Then the proximal end of the guide wire is inserted into the introducer distal tip 16a1 of the introducer 16. Saline or a suitable bio-compatible fluid is provided to the introducer valve 16d to remove air in the introducer 16, and then introducer tip 16a1 (and preferably both the introducer and dilator) is inserted into the patient and advanced along the guide wire until it reaches the desired position in the vena cava or iliac vessel. Positioning of the introducer tip 16a1 within the vein at the site for delivering the filter may be confirmed by fluoroscopy, aided by the radio-opaque markers on or within the introducer 16. The dilator tube 18b is then inserted through the introducer body 16c until the dilator hub 18a is snap-fitted onto the coupling port 16b of the introducer 16. Contrasting agent or dye may also be provided to the ports 18d of the dilator tube 18b via the dilator body 18a to provide for visual imaging of the introducer tip 16a1 via suitable fluoroscopic imaging equipment. The guide wire and the dilator 18 can be removed once the user or physician has determined that the introducer tip 16a1 is at the desired location in the vein or vessel.

Saline infusion may be supplied to the Touhy-Borst Adapter 10. The filter 14, which is pre-stored in the storage tube 15, may be coupled to the coupling port 16b via the snap-fitting, and saline can be permitted to flow through the storage tube 15 to improve lubricity between various components of the delivery system 100. Alternatively, the saline may be chilled during portions of the procedure in order to help maintain the filter 1 and push rod assembly 60 components below the super-elastic shape memory alloy martensitic-to-austenitic transition temperature so that the positioning members, anchoring members and push wire portion 67 remain flexible. Similarly, the saline may be warmed during portions of the procedure, such as just prior to releasing the filter into the vein, to help raise the filter 1 and filter positioning assembly 70 components above the martensitic-to-austenitic transition temperature, causing the filter to seek its annealed shape. The introducer 16, storage tube 15 and elongated push rod assembly 60 are preferably held in a linear configuration to avoid kinking and minimize friction. The filter 1 is physically advanced from the storage tube 15 through the introducer 16 to a position near the distal tip 16a1 of the introducer 16. The advancement of the filter 1 can be accomplished by maintaining the introducer 16 stationary while pushing on the handle 61 of the push rod assembly 60 in the distal direction. The filter 1 is maintained inside the introducer 16, i.e., undeployed at this point. Markings on the push rod assembly 60 may permit the clinician to know the position of the filter 1 with respect to the end of the introducer 16. Additionally, fluoroscopy may be used to track the position of the filter 1 within the introducer 16 and with respect to the patient. When the filter hub 2 approaches the distal end of the introducer 16, as is shown in FIG. 15, the filter is ready to be deployed. At this point, the filter delivery steps described above with reference to FIGS. 15-20 will be implemented.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it has the full scope defined by the language of the following claims, and equivalents thereof.

What is claimed is:

1. A blood filter and delivery apparatus for delivering a blood filter into a blood vessel, the vessel having a wall and a centerline, the apparatus comprising:
    a) a blood filter including a plurality of filter members, a proximal filter end, and a distal filter end
    b) a catheter having proximal and distal ends, the distal end being a free end portion with an opening, the catheter having a catheter wall with an inner surface surrounding a catheter lumen;
    c) a filter positioning assembly situated with the filter within the catheter lumen to define a stored position, the filter positioning assembly including a plurality of positioner members, each of the plurality of positioner members having a distal end that is connected to one or more filter members of the filter within the catheter lumen in said stored position;
    d) wherein in said stored position, the filter is positioned closer to the filter opening than the positioning assembly;
    e) a pusher that engages the positioning assembly and filter inside the lumen in said stored position, wherein the positioning assembly and filter are movable from said stored position within the catheter lumen, to a preliminary dispensed position, and to a fully deployed position;
    f) wherein in said preliminary dispensed position, some of the filter members and some of the positioning members engage the vessel wall while at least a portion of some of the filter members remain inside the catheter lumen; and
    g) wherein in said fully deployed position all the filter members of the filter are deployed in the vessel by at least partially retracting the plurality of positioner members with the catheter.

2. The blood filter delivery apparatus of claim 1, further comprising a hub coupled to the plurality of positioner members, said hub defining the filter distal end, the positioner members being in between the hub and the catheter open end in the stored position.

3. The blood filter delivery apparatus of claim 2, wherein the hub includes a radio-opaque material.

4. The blood filter delivery apparatus of claim 2, wherein the hub includes at least one spline configured to retain the plurality of filter members.

5. The blood filter delivery apparatus of claim 2, wherein the hub, spline and plurality of positioner members are formed integrally.

6. The blood filter delivery apparatus of claim 2, wherein the hub has a central hub lumen.

7. The blood filter delivery apparatus of claim 1, wherein in the preliminary dispensed position the plurality of positioner members are configured to extend radially to define a catheter centerline as the filter positioning assembly and a portion of the filter exit an end of the catheter and wherein the plurality of positioner members press against a wall of the blood vessel.

8. The blood filter delivery apparatus of claim 7, wherein the positioner members locate the end of the catheter substantially along the catheter centerline so as to further locate the end of the catheter centrally within the blood vessel.

9. The blood filter delivery apparatus of claim 4, wherein in an installed position the plurality of filter members are unconstrained by the catheter after the end of the catheter is positioned substantially along the centerline.

10. The blood filter delivery apparatus of claim 1, wherein the plurality of positioner members are of a Nitinol material.

11. The blood filter delivery apparatus of claim 1, wherein the filter positioning assembly has a longitudinal axis, and further comprises an extension wire oriented along the longitudinal axis and configured to contact a hub of the filter when the plurality of filter members are retained by the plurality of positioner members.

12. The blood filter delivery apparatus of claim 1, wherein the pusher includes an elongated push rod coupled to the filter positioning assembly.

13. The blood filter delivery apparatus of claim 1, wherein the plurality of positioner members each have a constant cross section over a majority of its length.

14. The blood filter delivery apparatus of claim 1, wherein the plurality of positioner members each have a proximal end and a distal end to define a length therebetween, at least one positioner member having a variable cross section over a majority of the length.

15. The blood filter delivery apparatus of claim 14, wherein the at least one-positioner member has a cross section at the proximal end greater than the cross section at the distal end.

16. The blood filter delivery apparatus of claim 14, wherein the at least one positioner member has a cross section at the proximal end less than the cross section at the distal end.

17. The blood filter delivery apparatus of claim 1, wherein the plurality of positioner members are curved with a constant radius of curvature over a majority of their length.

18. A blood filter and delivery assembly for delivering a blood filter to a blood vessel having a blood vessel wall, comprising:
    a) a storage tube having proximal and distal end portions, a tube bore, and a distal open end at said distal end portion;
    b) a blood filter having a filter proximal and a filter distal end and positioned within the storage tube bore to provide a storage position wherein the filter distal end is closer than the filter proximal end to the storage tube distal open end, the blood filter including a plurality of filter members having free end portions that are positioned proximally in said storage position;
    c) a filter positioning assembly positioned within the storage tube bore in said storage position, the filter positioning assembly including a plurality of positioner members that extend distally and connect to the free end portions of the plurality of filter members in said storage position that places the filter closer to the distal open end and the positioning assembly farther from the distal open end relative to said filter;
    d) a pusher that engages and pushes the connected positioner assembly and filter from the lumen toward the vessel via the distal open end into a preliminary dispensed position, and into a fully deployed position;
    e) wherein in said preliminary dispensed position, the positioner members engage the vessel wall while at least a portion of some of the filter members appendages remain in the tube bore; and f) wherein in said fully deployed position all the filter members of the filter are deployed in the vessel by at least partially retracting the plurality of positioner members with the catheter.

19. The blood filter delivery apparatus of claim 18, wherein the pusher includes an elongated push rod coupled to the filter positioning assembly.

20. A push rod assembly for use in delivering a filter into a blood vessel, the vessel having a wall, the assembly comprising:
   a) a catheter having a catheter bore and a distal open end;
   b) a blood filter having proximal and distal filter ends and a plurality of anchor members having anchor end portions at said proximal filter end;
   c) a push rod extending along a longitudinal axis from a first end to a second end;
   d) a handle disposed proximate the first end;
   e) a filter positioning assembly disposed at the second end, the filter positioning assembly having a longitudinal axis and including:
      a hub; and
      a plurality of positioner members coupled to the hub, each positioner member having a positioner end extending distally, wherein each of the plurality of positioner members is curved and oriented so that the positioner members extend away from the longitudinal axis when unconstrained, and the positioner members are configured to extend toward the longitudinal axis so that the positioner members connect to and retain the plurality of anchor members when the positioner members and blood filter are positioned within the catheter in a storage position;
   f) the anchor end portions being the most proximate portion of the filter;
   g) the positioner ends being the most distal portion of the filter positioning assembly;
   h) wherein the filter and positioner members are movable to a preliminary dispensed position and to a fully deployed position;
   i) wherein in said preliminary dispensed position, the positioner ends engage the vessel wall, wherein at least a portion of some of the anchor members remain in the catheter bore proximally of said catheter distal open end; and
   j) wherein in said fully deployed position all the filter members of the filter are deployed in the vessel by at least partially retracting the plurality of positioner members with the catheter.

21. The push rod assembly of claim 20, wherein the plurality of positioner members are configured to press against a wall of the blood vessel as the filter positioning assembly and filter exit an end of the catheter.

22. The push rod assembly of claim 20, wherein the plurality of positioner members comprise Nitinol material.

23. The push rod assembly of claim 20, further comprising an extension wire oriented along the longitudinal axis and configured to contact a hub of the filter when the plurality of anchor members are retained by the plurality of positioner members.

24. The push rod assembly of claim 20, wherein the hub of the positioning assembly includes a radio-opaque material.

25. The push rod assembly of claim 20, further comprising a storage tube encompassing the filter positioning assembly and the blood filter.

26. The push rod assembly of claim 20, wherein the plurality of positioner members have a constant cross section over a majority of their length.

27. The push rod assembly of claim 20, wherein the plurality of positioner members have a variable cross section over a majority of their length.

28. The blood filter delivery apparatus of claim 20, wherein the plurality of positioner members are curved with a constant radius of curvature over a majority of their length.

29. A blood filter delivery apparatus for delivering a blood filter into a blood vessel, the vessel having a wall, the apparatus comprising:
   a) a blood filter including a plurality of anchor members and having proximal and distal end portions;
   b) a catheter having proximal and distal ends, a bore, and a distal catheter opening at the distal end of the catheter;
   c) a filter positioning assembly situated within the catheter bore, the filter positioning assembly including a plurality of positioner members, each having a positioner distal end and a hub defining a plurality of splines, each of the splines being configured to cooperate with and retain the plurality of anchor members within the catheter when the ends of the positioner members are the most distal portion of the positioning assembly disposed within the catheter;
   d) wherein the anchor members have proximal free ends that are the most proximal portion of the blood filter;
   e) wherein in an initial, partially dispensed position the distal ends of the positioner members engage the vessel wall while at least a portion of some of the anchor members are located in the catheter bore proximally of said distal catheter opening; and
   f) wherein in a fully deployed position all the filter members of the filter are deployed in the vessel by at least partially retracting the plurality of positioner members with the catheter.

* * * * *